(12) United States Patent
Baid

(10) Patent No.: US 12,029,869 B2
(45) Date of Patent: *Jul. 9, 2024

(54) INTRAVENOUS CATHETER APPARATUS WITH SAFETY FUNCTION AND PRESSURE CONTROLLED VALVE ELEMENT

(71) Applicant: POLY MEDICURE LIMITED, Faridabad-Haryana (IN)

(72) Inventor: Rishi Baid, New Dehli (IN)

(73) Assignee: POLY MEDICURE LIMITED, Faridabad (IN)

(*) Notice: Subject to any disclaimer, the term of this patent is extended or adjusted under 35 U.S.C. 154(b) by 202 days.

This patent is subject to a terminal disclaimer.

(21) Appl. No.: 17/472,346

(22) Filed: Sep. 10, 2021

(65) Prior Publication Data

US 2021/0402154 A1  Dec. 30, 2021

Related U.S. Application Data

(63) Continuation of application No. 15/768,754, filed as application No. PCT/IB2017/050499 on Jan. 31, 2017, now Pat. No. 11,116,944.

(30) Foreign Application Priority Data

Aug. 1, 2016 (IN) .............................. 201611026278

(51) Int. Cl.
  *A61M 25/06* (2006.01)
  *A61M 5/32* (2006.01)
  (Continued)

(52) U.S. Cl.
  CPC ...... *A61M 25/0606* (2013.01); *A61M 5/3273* (2013.01); *A61M 25/0097* (2013.01);
  (Continued)

(58) Field of Classification Search
  CPC .......... A61M 25/0606; A61M 25/0097; A61M 25/0618; A61M 5/3273; A61M 39/06;
  (Continued)

(56) References Cited

U.S. PATENT DOCUMENTS 5,603,702 A    2/1997 Smith et al.
11,116,944 B2* 9/2021 Baid ................. A61M 25/0097
  (Continued)

FOREIGN PATENT DOCUMENTS

CN    203694357 U    7/2014
EP     1545681 A1    6/2005
  (Continued)

OTHER PUBLICATIONS

International Search Report and Written Opinion for International Patent Application No. PCT/IB2017/050499, dated Jun. 2, 2017.

*Primary Examiner* — Theodore J Stigell
*Assistant Examiner* — Nidah Hussain
(74) *Attorney, Agent, or Firm* — Bradley Arant Boult Cummings LLP; Henry B. Ward, III

(57) ABSTRACT

The invention relates to an intravenous catheter apparatus comprising: a catheter hub arranged at a proximal end of a catheter tube, the catheter hub having an inner surface defining a chamber; a needle defining an axial direction and having a needle tip, the needle extending through the chamber and the catheter tube when in a ready position; a needle guard slidably arranged on the needle and at least partially received in the chamber when the needle is in the ready position, the needle guard including a base portion and first and second arms extending from the base portion, wherein the first arm is deflected radially outwards by the needle against a restoring force when the needle is in the ready position whereby the needle guard is brought into retaining contact with the catheter hub; and wherein the catheter
(Continued)

apparatus includes a valve which separates a distal space arranged in distal direction from the valve from a proximal space arranged on proximal direction from the valve. The invention further provides that the valve opens based on a pressure differential between the pressure prevailing in the distal space and the pressure prevailing in the proximal space.

30 Claims, 23 Drawing Sheets

(51) Int. Cl.
 *A61M 25/00* (2006.01)
 *A61M 39/06* (2006.01)
(52) U.S. Cl.
 CPC ..... *A61M 39/06* (2013.01); *A61M 2025/0078* (2013.01); *A61M 25/0618* (2013.01); *A61M 2039/062* (2013.01); *A61M 2039/064* (2013.01)

(58) Field of Classification Search
 CPC .... A61M 2025/0078; A61M 2039/062; A61M 2039/064
 USPC .................................................... 604/167.04
 See application file for complete search history.

(56) References Cited

U.S. PATENT DOCUMENTS

| | | |
|---|---|---|
| 2009/0264832 A1 | 10/2009 | Dikeman et al. |
| 2014/0276433 A1 | 9/2014 | Woehr et al. |
| 2014/0276434 A1 | 9/2014 | Woehr |
| 2015/0306349 A1* | 10/2015 | Bonnal ............. A61M 25/0097 604/272 |

FOREIGN PATENT DOCUMENTS

| | | |
|---|---|---|
| EP | 1656179 A1 | 4/2006 |
| WO | 9000071 A1 | 1/1990 |
| WO | 2004082757 A1 | 9/2004 |
| WO | 2015104336 A1 | 7/2015 |

* cited by examiner

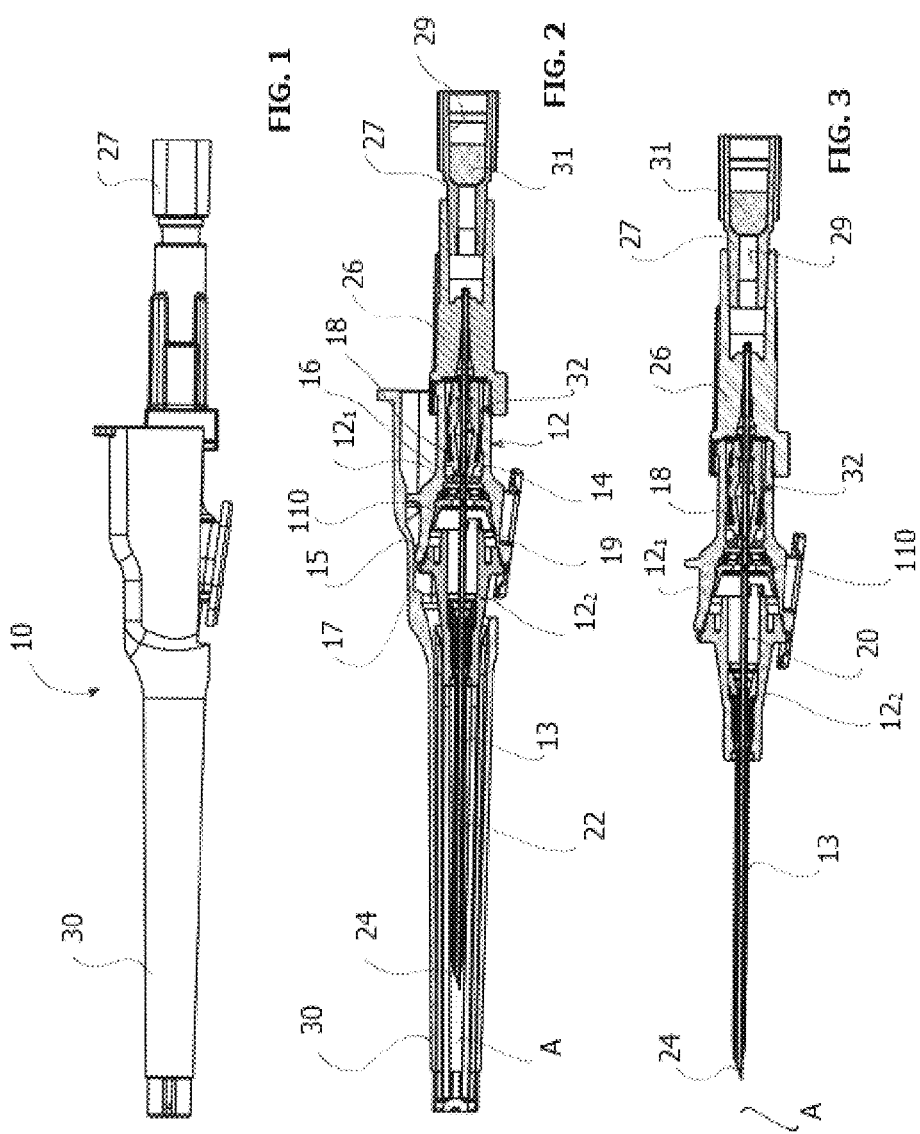

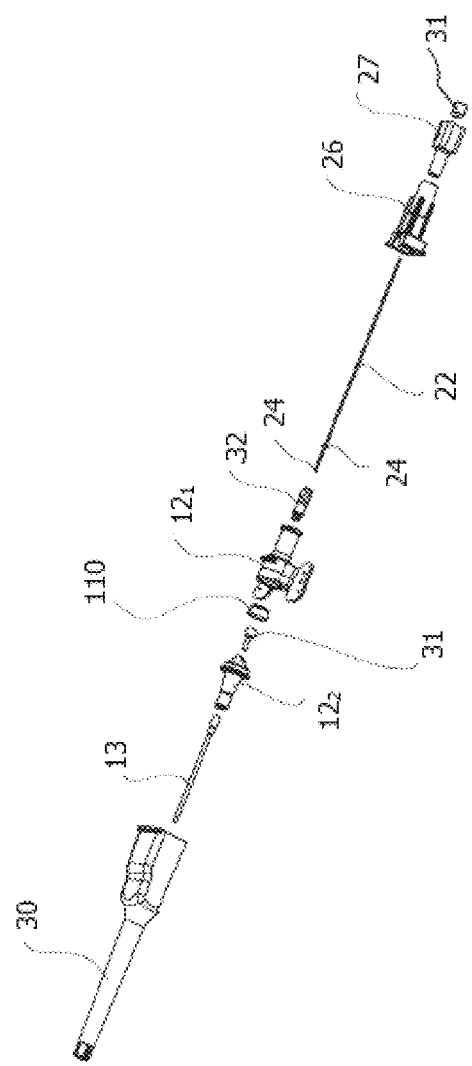

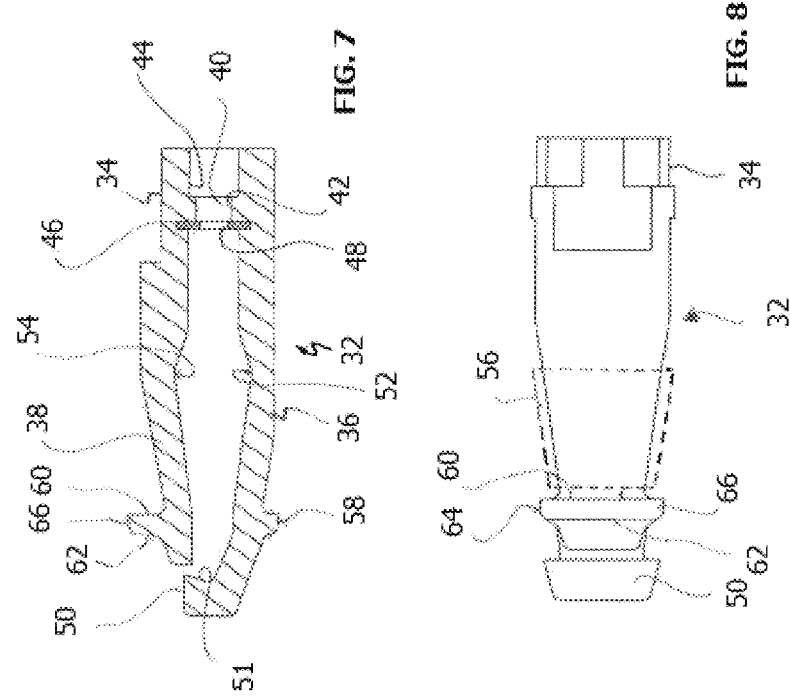

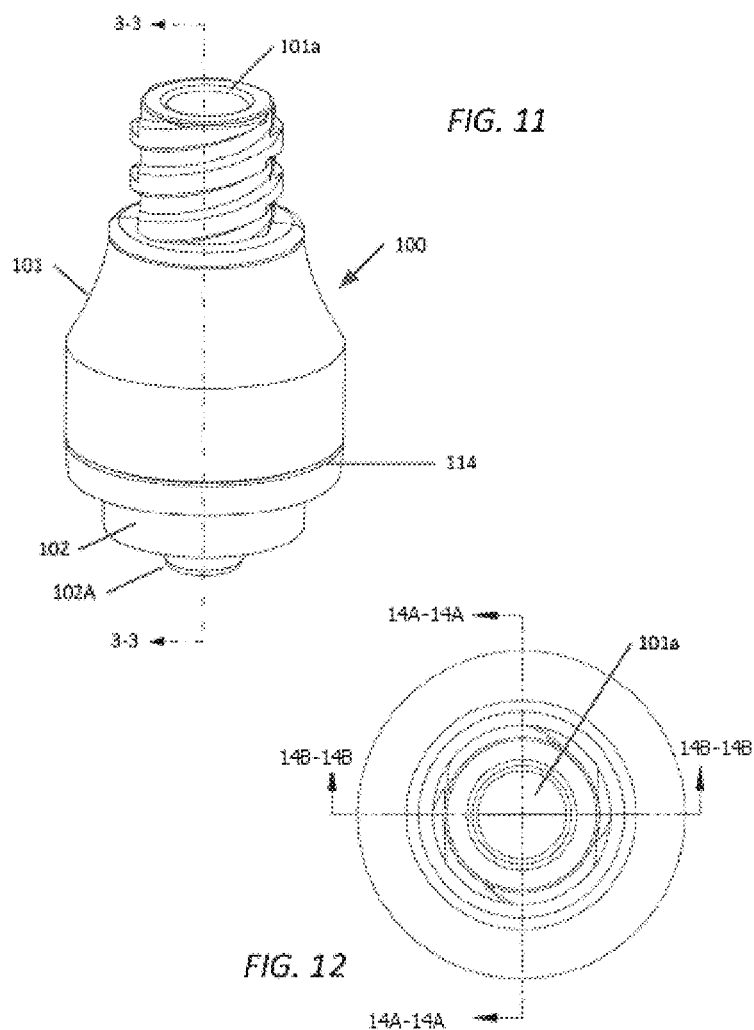

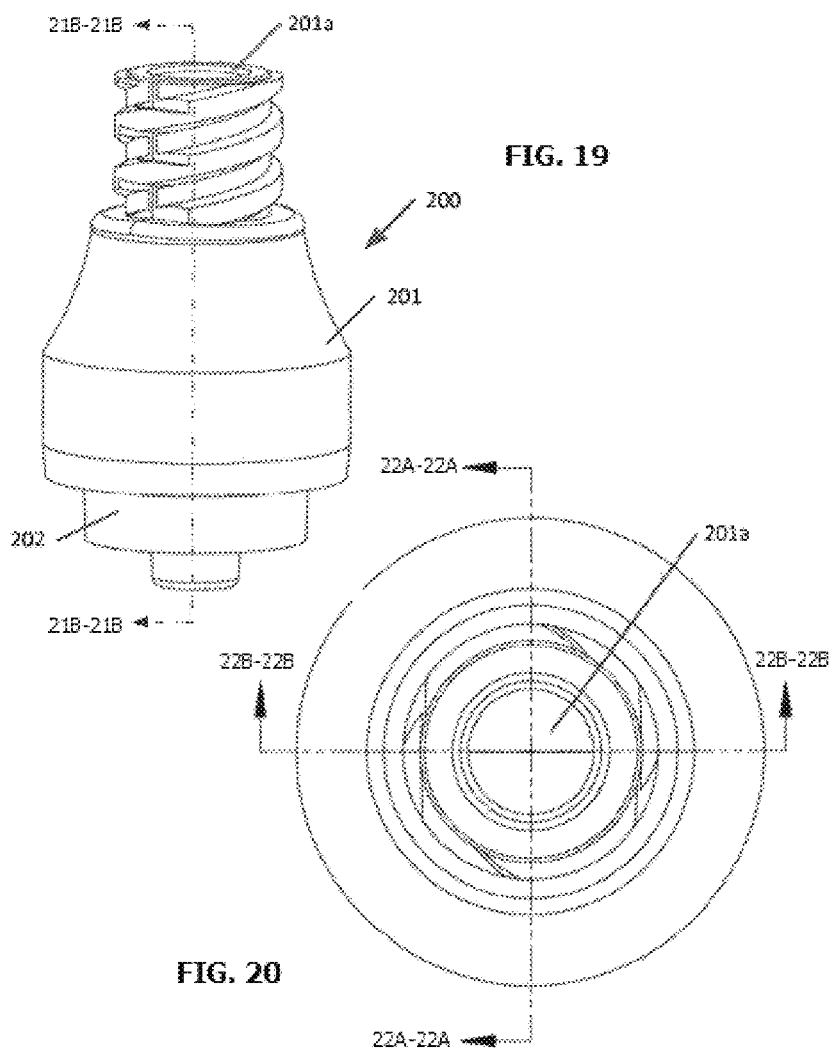

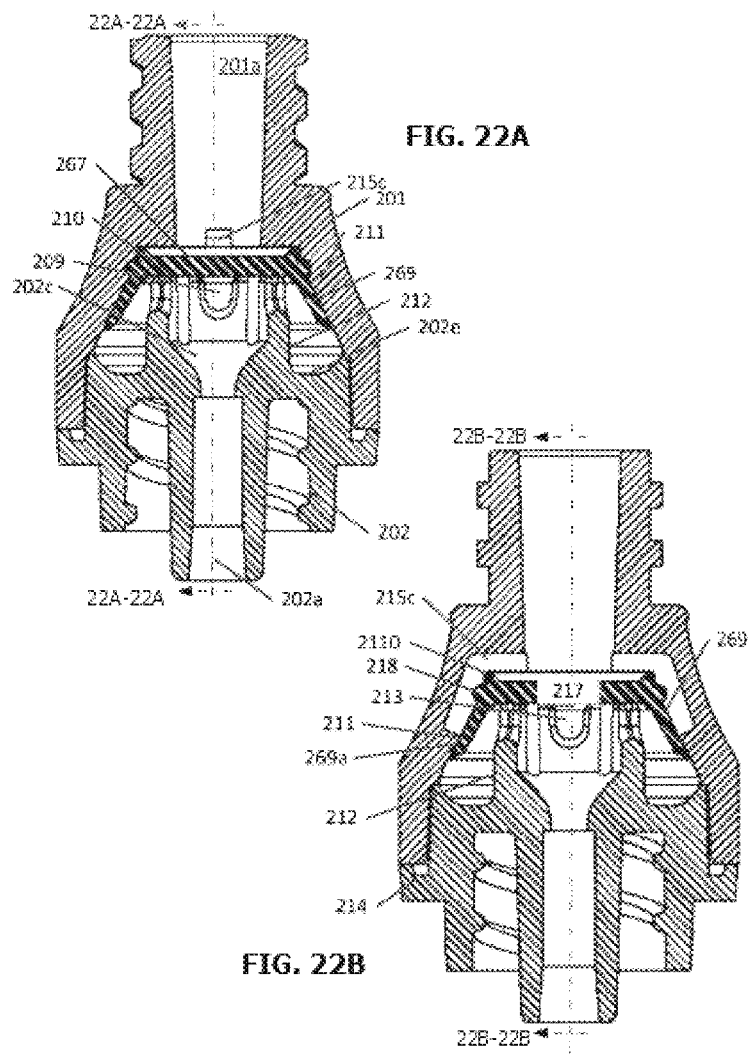

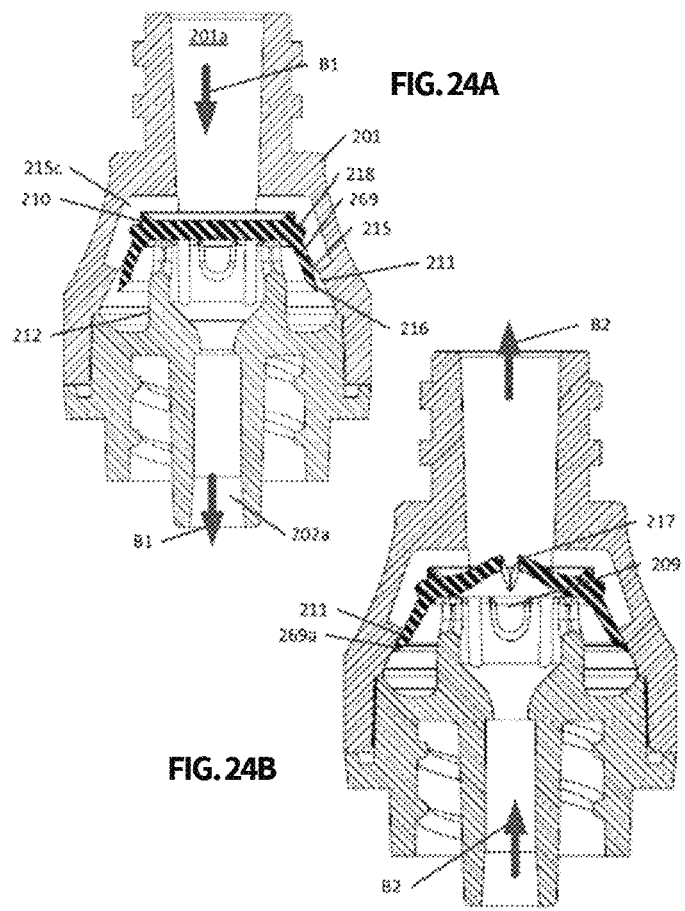

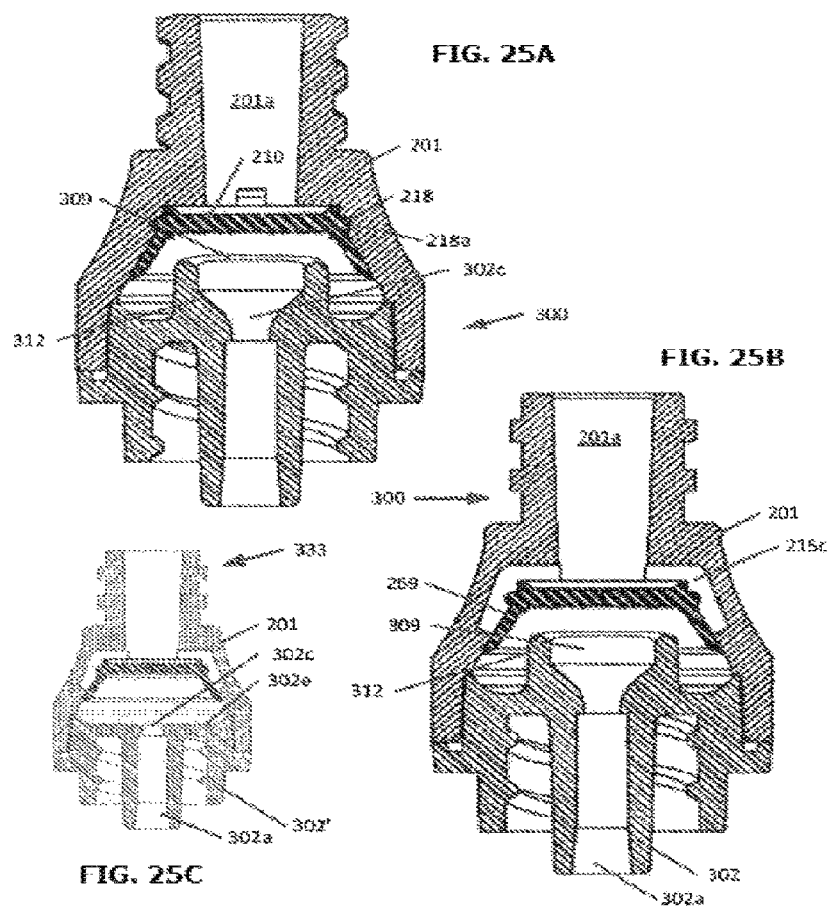

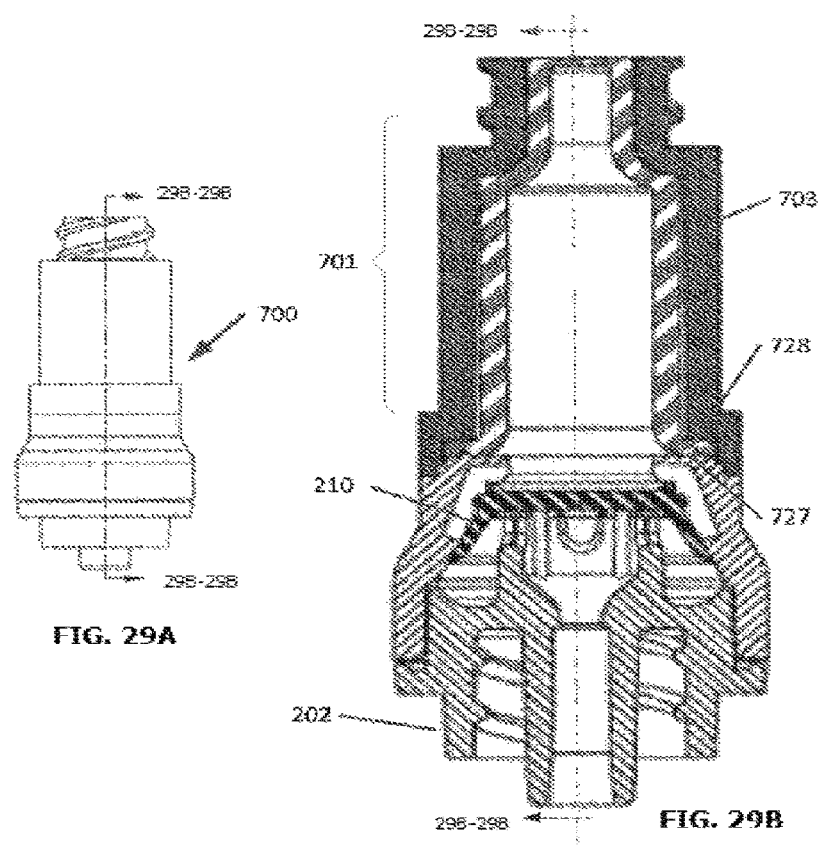

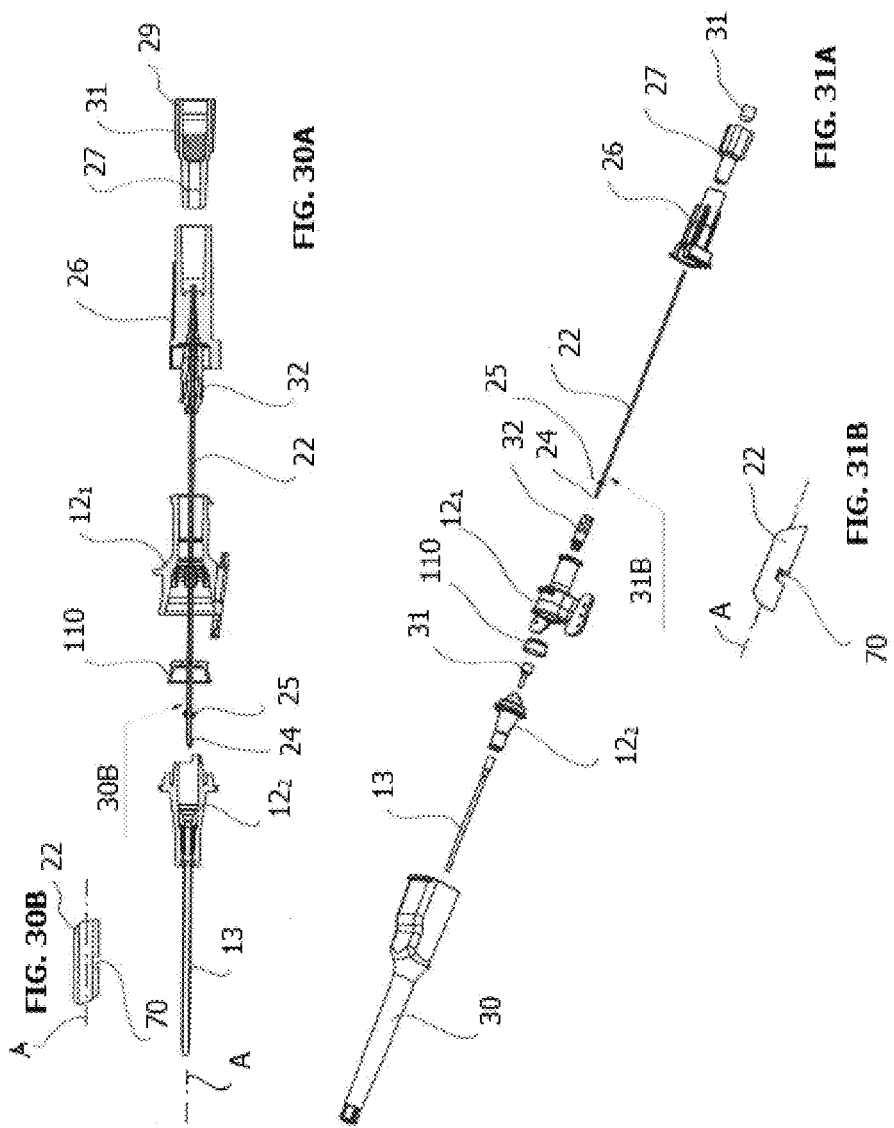

INTRAVENOUS CATHETER APPARATUS WITH SAFETY FUNCTION AND PRESSURE CONTROLLED VALVE ELEMENT

SUBJECT MATTER OF THE INVENTION

The invention relates to an intravenous catheter apparatus, comprising: a catheter hub arranged at a proximal end of a catheter tube, the catheter hub having an inner surface defining a chamber; a needle defining an axial direction and having a needle tip, the needle extending through the chamber and the catheter tube when in a ready position; a needle guard slidably arranged on the needle and at least partially received in the chamber when the needle is in the ready position, the needle guard including a base portion and first and second arms extending from the base portion, wherein the first arm is deflected radially outwards by the needle against a restoring force when the needle is in the ready position whereby the needle guard is brought into retaining contact with the catheter hub; and wherein the catheter apparatus includes a valve which separates a distal space arranged in distal direction from the valve from a proximal space arranged on proximal direction from the valve.

RELATED ART

An intravenous catheter apparatus of this kind is generally known. The needle guard serves to prevent a person handling the intravenous catheter apparatus from accidentally coming into contact with the needle tip after placement of the catheter tube in and subsequent removal of the needle from a patient's vein. Thereby, the intravenous catheter apparatus helps to avoid unwanted transmission of blood borne diseases.

Moreover, blood reflux into central line and other types of intravenous catheters can lead to intraluminal thrombosis, creating a full or partial occlusion of the IV access device. Such occlusions can interfere with IV therapy, provide a nutrient-rich area for pathogenic bacteria, or be detached from the catheter, leading to venous thrombosis. Even in cases where intraluminal thrombosis does not lead to further health complications, such a condition requires the replacement of the catheter, a procedure which can be both time consuming and lead to injury at the removal site and the new introduction site.

Flow valves for intravenous medical devices are already known from different prior art documents, e.g. US 2009/0264832 A1, WO 90/00071 A1, EP 1 656 179 A1 or WO 2004/082757 A1. However, the flow valves known from these documents are relatively complicated in their structure and difficult to manufacture. Moreover, these documents do not include any hint on safety features including a needle guard.

Moreover, document EP 1 545 681 A1 describes a safety IV catheter having a valve arrangement. However, this valve arrangement requires mechanically activated components for actuating the valve. This leads to a complicated structure, which is difficult to manufacture and assemble and which does not provide a reliable function.

OBJECT OF THE INVENTION

It is an object of the present invention to provide an intravenous catheter apparatus which provides better protection against accidental pricking by the needle tip and which is inexpensive to manufacture at the same time.

SUMMARY OF THE INVENTION AND GENERAL DESCRIPTION OPTIONAL FEATURES OF THE INVENTION

The object is solved by an intravenous catheter apparatus in accordance with claim 1.

The intravenous catheter apparatus of the invention comprises a catheter hub arranged at a proximal end of a catheter tube and having an inner surface defining a chamber; a needle defining an axial direction and having a needle tip, wherein the needle extends through the chamber and the catheter tube when in a ready position; a needle guard slidably arranged on the needle and received in the chamber when the needle is in its ready position, the needle guard including a base portion and first and second arms extending from the base portion, wherein the first arm is deflected radially outwards by the needle against a restoring force when the needle is in its ready position whereby the needle guard is brought into retaining contact with the catheter hub; and retaining means for retaining the needle guard in the chamber as long as the first arm is in its deflected state. The retaining means include a first disc-like retaining protrusion provided on the first arm and a retaining depression formed in the inner surface of the catheter hub and adapted to receive the retaining protrusion. Moreover, the catheter apparatus includes a valve which separates a distal space arranged in distal direction from the valve from a proximal space arranged on proximal direction from the valve, wherein the valve opens based on a pressure differential between the pressure prevailing in the distal space and the pressure prevailing in the proximal space.

In one embodiment, the catheter hub of the intravenous catheter apparatus comprises a main body and extending in an axial direction. The main body has a distal end and a proximal end. A catheter is attached to the main body at the distal end of the main body. A port extends from the main body in a direction generally perpendicular to the axial direction. Wings can be provided at the main body opposite from the port. The main body defines a chamber extending from the proximal end towards the distal end.

By providing the intravenous catheter according to the invention, on the one hand, the safety function provides a safe covering of the needle tip as soon as the needle is in its retracted position. Moreover, the pressure activated valve allows a safe and reliable control of the fluid flow through the catheter apparatus depending on the actual demands for the therapy of a patient. The pressure activated valve is easy to manufacture and reliable and easy to handle in practical use.

According to one embodiment of the present invention, the valve comprises a housing having an first opening and a second opening; and an elastomeric member positioned in the housing, the elastomeric member comprising a thickness, a continuous peripheral wall projecting from the thickness; and a slit extending through the thickness, a continuous portion of the peripheral wall creating a continuous sealable contact with the housing and partitioning the housing into an upper section and a lower section, the elastomeric member configured such that upon creating a pressure differential between the upper section and the lower section of the housing causes either: (i) the peripheral wall to deflect from the housing permitting fluid flow around the elastomeric member; or (ii) the slit to open permitting fluid flow through the elastomeric member.

Moreover, according to a further embodiment of the invention, the valve further comprises a support positioned in the housing and surrounded by the peripheral wall, the support configured to provide fluid communication between the first opening and the second opening. In another aspect, alone or in combination with any of the previous aspects mentioned above, the support member is received by or integral with the housing. In another aspect, alone or in combination with any of the previous aspects of the first embodiment, the support member comprises a plurality of spaced apart columns arranged about the second opening, the distal ends of the plurality of columns surrounded by the peripheral wall. In another aspect of the present invention, the support member comprises an annular wall arranged around the second opening, the annular wall having at least one fluid flow passage providing fluid communication between the lower section and the second opening.

In another aspect of the present invention, the second opening comprises a conduit that extends into the housing and is surrounded the peripheral wall. In another aspect, a portion of the conduit extending into the housing is of a larger internal diameter than the conduit extending external to the housing.

In another aspect of the present invention, a portion of housing is tapered and a distal portion of the peripheral wall tapers in sealable contact therewith.

In another aspect of the present invention, the upper portion of the housing comprises an interior wall, the interior wall comprising at least one recessed channel therein and extending substantially along the longitudinal axis of the housing, wherein deflection of the peripheral wall from the housing substantially corresponds to the placement of the at least one recessed channel.

In another aspect of the present invention, the housing comprises two or more components sealably connectable to form a fluid tight assembly.

In another aspect of the present invention, the elastomeric element comprises a top surface and a bottom surface separated from the top surface by the thickness; and the peripheral wall has a second thickness, and the peripheral wall projects from the bottom surface. In another aspect, alone or in combination with any of the previous aspects of the first embodiment, the second thickness is less than the thickness between the top and bottom surfaces.

In another aspect of the present invention, the elastomeric member further comprises a continuous lateral protrusion along the peripheral edge of the thickness, and the housing is configured with a corresponding recess to receive the continuous lateral protrusion and to provide a radial stress to the surface of the elastomeric member. In another aspect of the present invention, the elastomeric member further comprises one or more vertical protrusions on the top surface, the housing being configured to provide a normal stress to the one or more vertical protrusions. In another aspect of the present invention, the thickness is concave, convex, or concave and convex on opposing sides of the thickness.

In another aspect of the present invention, the elastomeric member is annular, oval, cylindrical, hemispherical, or cup-shaped. In another aspect, alone or in combination with any of the previous aspects of the first embodiment, the elastomeric member is conical frustum-shaped.

In another aspect of the present invention, the top surface of the elastomeric member has one or more fluid channels terminating at the peripheral edge.

In another aspect of the present invention, the slit opens at a threshold pressure greater than a threshold pressure required to deflect the peripheral wall from the housing.

In another aspect of the present invention, the slit, in combination with the first opening and the second opening, is configured to receive an elongated medical device through the housing, in particular the needle of the catheter apparatus. In another aspect of the present invention, the support is configured to receive and/or guide an elongated medical device through the housing, in particular the needle of the catheter apparatus. In another aspect of the present invention, the support in combination with the slit is configured to receive and/or guide an elongated medical device through the housing, in particular the needle of the catheter apparatus.

According to a further embodiment of the present invention, the housing of the valve is formed as a separate component or wherein the housing is part of the catheter hub. Thus, it is possible to arrange the valve in a separate component with a separate housing and to this separate component to the intravenous catheter. As an alternative the valve can be integrated within the intravenous catheter, e.g. within the catheter hub.

According to one embodiment of the present invention, the catheter hub is formed by at least two components, comprising a distal catheter hub portion holding the catheter tube, and a proximal catheter hub portion, wherein the at least two components are mounted to one another. As a matter of course, further components can be added. The respective distal catheter hub portion and proximal catheter hub portion may be in direct contact with one another or further components may be arranged in between. In this regard, it is possible according to the present invention that one of the distal catheter hub portion and the proximal catheter hub portion includes a female connecting section and wherein the other of the distal catheter hub portion and the proximal catheter hub portion includes a male connecting section fitting into the female connecting section.

In order to connect the distal catheter hub portion and the proximal catheter hub portion with one another, the male connecting section and/or the female connecting section can be formed with a thread or a snap-fit arrangement fitting into one another. Alternatively or in addition to providing such arrangements it is possible to glue, weld or otherwise fix these components to one another.

According to another embodiment of the present invention, the proximal catheter hub portion includes a first proximal catheter hub wall forming said chamber. As mentioned above, the chamber is provided for receiving and holding the needle guard in the ready position. The mechanism for holding the needle guard in the ready position and for releasing the needle guard after its transition in the retracted state is described in detail below.

According to a further embodiment of the present invention regarding the arrangement of the valve, the elastomeric member is arranged in an internal space formed by the distal catheter hub portion or by the proximal catheter hub portion or by the distal and the proximal catheter hub portion.

Furthermore, in regard to the valve arrangement it is possible according to the present invention that the support member is formed as a separate element or integrally formed either with the distal catheter hub portion or the proximal catheter hub portion. Integrating the support member allows further simplification of the structure of the present invention. Thereby, the number of parts can be reduced and assembling the intravenous catheter apparatus according to the invention is further facilitated.

In regard to the needle guard, the present invention further provides that the second arm can be deflected radially inwards when the needle tip is received between the arms. Moreover it is possible that the first and second arms are made of a resilient material. According to a preferred embodiment of the present invention in regard to the needle guard the first and second arms are made of a plastic material. According to a further embodiment of the needle guard, the first and second arms are integrally formed with the base portion.

Moreover, the needle guard according to the present invention can further provide that the restoring force is created by at least one of an elastic property of the first arm and an additional tension element at least partly surrounding the arms.

As a further aspect of the needle guard, the present invention can provide that the first arm is longer than the second arm. In addition to that, it is possible that the first arm has a distal end section having an undercut for catching the needle tip. Moreover, according to another aspect of the invention, the distal end section is angled towards the second arm and overlaps the second arm.

According to another aspect of the invention, the catheter hub may further comprise retaining means for retaining the needle guard in the chamber as long as the first arm is in its deflected state, the retaining means including a first disc-like retaining protrusion provided on the first arm and a retaining depression formed in the inner surface and adapted to receive the retaining protrusion. In this regard, according to the invention, it is further possible that the retaining protrusion has generally parallel proximal and distal faces and/or a convex, in particular part-cylindrical, peripheral surface.

Moreover, according to a further aspect of the present invention, a second disk-like retaining protrusion is arranged on the second arm and adapted to engage with the retaining depression.

According to a further aspect of the present invention, wherein the needle guard comprises a tension element at least partly surrounding the arms in a region proximal of the first retaining protrusion or applying a linear biasing force biasing the arms together.

According to a further embodiment of the present invention, the needle includes an opening closed the needle tip, wherein the distance between the needle tip and the opening is arranged such that the opening is covered by the catheter hub when the needle is in the ready position. Using such an opening, the medical practitioner receives immediate feedback whether the application to the patient was successful by a so-called flashback feature. The flashback feature provides that a small amount of blood pours out of the opening into the transparent catheter tube under the pressure of patient such that it becomes immediately visible whether the medical practitioner was successful in introducing the needle tip into the vein of the patient.

In regard to this aspect of the present invention, it is further possible that the opening is formed by a longitudinal slit extending with its longitudinal direction in parallel with or transverse to a longitudinal axis of the needle. Further shapes of the opening are also possible. However, forming a longitudinal slit provides an easy and simple way of manufacturing the opening.

According to a further aspect of the present invention the needle includes a needle feature close to its needle tip changing the cross-sectional shape of the needle. Such a feature can be an enlargement of the cross section of the needle, like a surrounding bump or rip formed on the outer circumferential surface of the needle shaft or formed by a local protrusion of added material provided at one particular outer circumferential part of the needle shaft. Alternatively and easier to manufacture, the needle feature can be formed by a local crimp providing that the needle is locally squeezed and deformed such that it has an oval cross-section which does not fit through the circular opening within the needle guard.

In this regard, the invention may further provide that the needle guard includes an opening with a predetermined diameter interacting with the needle feature such that it prevents the retraction of the needle out of the needle guard when the needle is in the retracted position. According to this aspect of the invention, it is possible that the opening of the needle guard interacting with the needle feature is integrally formed in the needle guard or formed by an a metal or plastic washer. Such an additional component like a metal or plastic washer can be co-molded with the the needle guard during manufacturing.

In a further embodiment, a method of controlling flow direction through the intravenous catheter apparatus according to the invention is provided. The method comprising: creating, in a device comprising the valve as defined in any of aspects of the first embodiment, a pressure differential between the upper section and the lower section of the housing; causing the peripheral wall to deflect from the housing and permitting fluid flow around the elastomeric member; or, in the alternative; causing the slit to open permitting fluid aspiration through the elastomeric member; wherein fluid flow direction through the device is controlled.

In regard to another aspect of this method, the pressure differential between the upper section, i.e. the proximal space, and the lower section, i.e. the distal space, of the housing is created by a negative pressure applied to the proximal section of the housing or by a positive pressure applied to the distal section of the housing so that the slit permits fluid flow therethrough. Furthermore, in regard to this method, the pressure differential between the proximal section and the distal section of the housing is created by a positive pressure applied to the proximal section of the housing so that the peripheral wall permits fluid flow around the elastomeric member.

In regard to another aspect of this method, the method further comprises introducing a flushing solution to the upper portion of the housing via the first opening; causing, by positive pressure, deflection of the peripheral wall from the housing; urging the flushing solution around the elastomeric member; redirecting fluid flow in the lower section of the housing; and cleaning at least a portion of the lower section of the housing.

In regard to a further aspect of this method, the cleaning further comprises preventing thrombus within the device after aspiration of biological fluid through the device or preventing bacterial growth within the device after aspiration. The method further may further comprise preventing reflux within the device.

The valve of the present disclosure, and in particular the intravenous catheter according to the present invention comprising the valve, reduce or eliminate reflux of blood into the distal tip of a vascular catheter. The valve has, by design, a high injection direction flow rate and a high internal fluid mixing, preventing un-flushable fluid volumes which could lead to bacterial colonization and catheter related blood stream infection (CRBSI). These two primary benefits are not readily available in the valves and devices present in the art.

The presently disclosed valve implemented within the intravenous catheter according to the present invention h can also be referred to as a "pressure activated valve," or, alternatively referred to as an "infusion patency valve". The valve comprises an elastomeric member configured to reside in a housing, the elastomeric member having a slit through a thickness, the elastomeric member further having a deflectable peripheral wall in interference contact with the housing interior so as to form a fluid-tight seal and to partition the housing into an upper and lower portion. Each partition having associated therewith an opening for fluid egress and ingress.

In one aspect, the disclosed valve allows for a low-head pressure delivery of fluids in one-direction to flow through the valve and openings the catheter apparatus. This type of fluid delivery is consistent with both continuous IV therapy and periodic delivery by injection or IV pump. When fluid, either through an attached Luer or other infusion device, is introduced into the proximal end of a device comprising the disclosed patency valve, a pressure differential is created between partitions in the housing. The pressure differential, in one state, deflects the peripheral wall surface of the elastomeric member, breaking a fluid-tight seal with the housing. This permits the flow of fluid around the elastomeric member and through this temporary junction, and introduces fluid into the other partition of the housing separated by the elastomeric member.

In one state, e.g., infusion, where there is a positive pressure differential formed between the upper and the lower partitions of the housing, the valve of the present disclosure provides a low valve cracking pressure. In addition to the low cracking pressure, the valve of the present disclosure further provides a low restriction to flow in the infusion direction (proximal to distal flow direction) which allows devices comprising the valve to be used with existing IV infusion systems. The low, but non-zero, cracking pressure of the valve described herein still prevents the ingress of air in the infusion direction when the valve is near the vertical level of the injection site. This is provided, among other things, by arranging flowing around the elastomeric member, and configuring the internal design of the housing so as to aid in valve flushability while providing for a high flow rate.

In another state, e.g., aspiration, where there is a negative pressure differential formed between the proximal and the distal partitions of the housing, the valve of the present disclosure provides a higher threshold cracking pressure than in the infusion direction. This configuration of the presently disclosed valve, among other things, prevents reflux of blood into the catheter lumen, typically resulting from a transient vacuum caused by the disconnection of a Luer, infusion accessory, or needle-free access valve. As a result of the design and configuration of the presently disclosed valve and devices comprising same, the prevention of blood reflux is provided and the risk of intraluminal thrombosis, and bacterial colonization or infection is therefore, reduced or eliminated. The cracking pressure of the presently disclosed valve in the aspiration direction is configured such that it is still low enough to permit the deliberate withdrawal of fluids using a syringe or vacuum tube, as is conventionally performed.

Another advantage of the presently disclosed valve or devices comprising same is the configuration of the valve within the device provides for high fluid mixing and/or flushing of blood-contacted surfaces. The fluid volume and/or velocity in the infusion direction is controlled so as to maximize fluid mixing in the partitioned space of the device. This high degree of mixing improves flushing of the valve, limiting dead volume that could otherwise lead to bacterial colonization from un-flushed nutrient-rich infusates.

The valve of the presently disclosed IV catheter apparatus is configured in one embodiment to be attached to the catheter, and is designed, among other things, to prevent the reflux of blood or other fluids into the lumen or lumens of the catheter apparatus. Inclusion of the valve, either alone or in a connector, can be used in combination with or integral with a medical device having a lumen, e.g., a vascular catheter, and can be configured for coupling with such devices or be configured for integration during the manufacture of the catheter, or later, at the point of use. One advantage of the presently disclosed valve and devices comprising same is that detachment of an accessing Luer-attached device from a proximal end of a device comprising the present valve, or detachment from a needle-free access valve attached to the proximal end of a device comprising the present valve will not cause the reflux of blood into the central line lumen(s). Moreover, a device comprising the present valve will still permit the withdrawal of fluids, such as blood or other biological fluids, through the lumen by an accessing syringe or vacuum vial (Vacutainer, e.g.).

In one aspect, the valve comprises a housing and an elastomeric member. In another aspect, the valve comprises a housing, and elastomeric member, and a support. The various aspects of the valve are now discussed in reference to exemplary embodiments and/or the accompanying drawings.

The housing comprising the valve can comprises a single component or be of a multi-component configuration of the IV catheter apparatus. In one aspect, the housing comprises an upper section and a lower section sealably connectable to the upper section to provide a watertight assembly. In another aspect, the housing comprises an upper section comprised of two or more parts that are sealably connectable to the lower section to provide a watertight assembly. The housing can be of a conventional plastic suitable for medical devices such as polycarbonate, polyester, cyclic olefinic copolymer, ABS, and the like.

The elastomeric member is configured to partition the housing into an upper and lower section. Generally, the elastomeric member can be annular, oval, cylindrical, hemispherical, cup-shaped or conical frustum-shaped. In one aspect, the elastomeric member can be cup-shaped or conical frustum-shaped with an internal cavity formed between its base and its surface. In one aspect, a horizontal or convex/concave surface with a peripheral wall projection from that surface forming a cup-shape or a conical frustum-shape can advantageously be used. The peripheral wall from such construction can be oval or round, or of another shape, provided a continuous fluid-tight seal can be cooperatively arranged with an interior portion of the housing and a portion of the outer surface of the peripheral wall so as to partition the housing into an upper and a lower portion, and provide flow direction functionality to the valve or the device. The peripheral wall can taper away from the surface it projects from or project normal thereto. Alternatively or in combination with a taper, the outer diameter of the peripheral wall and/or the surface it projects from can be greater than a corresponding inner diameter of the corresponding mating portion of the housing so as to provide the interference and/or fluidic seal to and/or partitioning of the housing. The taper angle of the peripheral wall can be greater than the taper of the interior wall of the housing to provide an interference relationship of an amount capable of facilitating a fluid-tight seal there between and to effectively partition the housing of the device into at least two sections. Alternatively or in combination with the above, the peripheral wall thickness can be tapered toward its distal end.

In one aspect, the elastomeric member comprises a conical frustum shape having a surface, the surface having a top surface and a bottom surface separated from the top surface by a first thickness, and the peripheral wall projecting away from the bottom surface has a second thickness, the peripheral wall forming a cavity that includes the bottom surface. The second thickness can be less than or equal to the first thickness. The surfaces can be concave and convex on opposing sides or can be concave or convex on one side only. The top surface of the elastomeric member can have one or more fluid channels terminating at its peripheral edge. Other features are described below and in the drawings.

According to another aspect, the elastomeric member comprises one or more slits through a thickness so as to open upon a pressure differential between the upper and lower sections of the housing, which can be created for example, by withdrawal of fluid from either distal ends of a device comprising the elastomeric member. The slit of the elastomeric member is configured to open at a threshold pressure greater than a threshold pressure required to deflect the peripheral wall from the housing. The housing is configured such that headspace above the elastomeric member and the inside surface of the upper housing provides sufficient clearance for the slit to open. In a first state, the slit is resistant to flow in the proximal to distal flow direction (e.g., infusion) in one aspect, which, among other things, limits the capacity of the slit to open in this flow direction. However, flow in another direction (e.g., aspiration) is permitted through the slit.

In one aspect, the elastomeric member has a generally flat or convex/concave top surface, having a conical frustum-shaped cavity that includes a bottom surface supported by one or more supports (e.g., protruding columns or a wall) that project aligned with the longitudinal axis of housing. The support(s) can be integral with the lower housing or can be placed in position during manufacturing. An interference fit of at least a portion of the elastomeric member is maintained by features on either the upper and/or or lower housings components and/or the elastomeric member. The elastomeric member may also be secured in place via an annular fitment or projection with or without said support(s) to position the elastomeric member during manufacturing and device use and/or provide a radial compressive stress to the slit (e.g., to adjust or control the slit cracking pressure). For example, the elastomeric member can comprises a continuous lateral protrusion along the peripheral edge of its top conical frustum surface, and the housing can be configured with a corresponding recess to receive the continuous lateral protrusion and to provide interference and/or a radial stress to the surface thickness of the elastomeric member. The continuous lateral protrusion can be of a thickness equal to or less than the thickness of the surface. In addition to or in combination with, the elastomeric member can comprise one or more vertical protrusions from its conical frustum top surface, the housing being configured and dimensioned to provide a normal stress to the one or more vertical protrusions for securing the elastomeric member during assembly or use.

In one aspect the elastomeric member is part of a valve assembly. The valve assembly can be configured for a variety of housing configurations designed for fluid coupling, such as two-way, three-way and four-way couplings. The valve assembly can comprise the elastomeric member and optional support configured for introduction into a housing. The assembly can be configured to adapt to a two-piece housing construct, either having a lower/upper housing, a two-piece housing separated along the longitudinal axis, or a combination thereof, e.g., a solid lower housing and a two-piece upper housing.

Withdraw of fluids through the infusion patency valve (fluid flow from in the distal to proximal direction) is restricted below the threshold cracking pressure of the slit(s) which are formed through the central axis of the elastomeric member. The threshold cracking pressure is designed to be high enough so that transient vacuum caused by the disconnection of a Luer, infusion accessory, or attached needle-free access valve, does not open the slit and hence, the valve to flow in that direction. However, the aspiration flow direction "cracking pressure" is designed to be low enough to permit the deliberate withdraw of fluid by syringe or vacuum tube, if needed. The design of the conical frustum-like section of the elastomeric member and its interference with the conical interior portion of the housing provides for one-way flow of fluid, operable in either direction, controlling the fluid flow in the housing between its openings with leak-free function and ease of use.

The valve and devices configured with this valve can be configured for passage of a medical device e.g., an introducer such as a guidewire or other medical device. Designs with the present valve can provide for an "over the guidewire" placement or replacement technique and eliminate or prevent bleed-back or air embolisms. In one aspect of the present disclosure each of the embodiments are exclusive of spring-actuated valve assemblies, or spring-actuated valve assemblies having an introducer valve within a cavity of the valve housing, or compression ring actuated valve assemblies. Of course, such devices can be used in combination with the presently disclosed valve. The valve embodiments disclosed herein eliminate the need for a triple layer design of a slit opening, followed by a hole, followed by another slit opening, for example. Indeed, in certain aspects, the present disclosure is devoid of pinching of the elastomeric member between halves of the housing for supporting the elastomeric member, whereas, instead, a design of the elastomeric member in cooperative relationship with the interior wall of the housing is employed. Likewise, the presently disclosed valve embodiments minimize dead space above and below the valve assembly and/or provides for effective flushing of any such dead space. Furthermore, the present valve embodiments avoid problems common to other configurations of pressure-actuated valves used in medical devices, such as: 1) leakage of fluids through "dome-like" septa having slits for two-way fluid transfer; 2) an inability to gravity feed through devices having a slit "trampolined" between walls of a housing; and 3) an inability to effectively flush the inside of the device with valves designed for two-fluid flow through the slit. The present valve, in contrast, provides for elimination of leakage, the ability to gravity feed, as well as improved flushing of the inside of the device comprising the valve. Moreover, additional advantages of the valve of the present disclosure includes the directional control of fluid flow through the device via passage either through or around the elastomeric member, the minimization of dead space and/or improved flushing capability, repeatable guidewire accessibility without failure or problems generally associated with known valved systems.

The elastomeric member can be fabricated from conventional thermoset rubbers (synthetic and non-synthetic). The elastomeric member is configured between the proximal and distal housings during manufacturing. The interference between the conical periphery of the elastomeric member and the conical portion of the proximal housing forms a normally closed valve. This interference, among other things, allows low pressure passage of liquids in one direction.

The design of the pressure activated/patency valve allows for the passage of a wire or cannula through the central axis of the device. This is helpful for placement of a PICC or CVC catheter, as well as a short peripheral IV catheter. Thus, the presently disclosed valve can serve to function as a "bloodless start" valve, thereby limiting exposure of blood to the clinician upon placement of the catheter. Upon insertion, the wire or needle cannula can be removed, the slit automatically closes upon its removal, and the caregiver is protected from excess exposure of blood. This may also keep the catheter hub more free of nutrient rich fluid to further protect the patient from possible infection of the site. The slit of the elastomeric member, in cooperation with the first opening and the second opening of the housing, can be configured to receive an elongated medical device through the housing. The housing may include a support or an inwardly tapered opening feeding into the second opening is configured to receive and/or guide an elongated medical device through the housing.

The above valve provides for a method of creating a pressure differential between the upper section and the lower section of a housing comprising the valve presently disclosed. This pressure differential causes either the peripheral wall to deflect from the housing and permitting fluid flow around the elastomeric member, or, in the alternative, causes the slit to open permitting fluid aspiration through the elastomeric member. In this method, fluid flow direction through the device is controlled. By way of example, the pressure differential between the upper section and the lower section of the housing is created by a negative pressure applied to the upper section of the housing or by a positive pressure applied to the lower section of the housing so that the slit permits fluid flow therethrough. In other example, the pressure differential between the upper section and the lower section of the housing is created by a positive pressure applied to the upper section of the housing so that the peripheral wall permits fluid flow around the elastomeric member.

The method further comprises introducing a flushing solution to the upper portion of the housing via the first opening and causing, by positive pressure, deflection of the peripheral wall from the housing. This results in the urging the flushing solution around the elastomeric member and under and in the cavity of the conical frustum-shaped elastomeric member, along with the redirecting of fluid flow in the lower section of the housing. This provides cleaning of at least a portion of the lower section of the housing. This cleaning prevents thrombus within the device after aspiration of biological fluid through the device and/or prevents bacterial growth within the device after aspiration.

The upper and lower housings and further components of the intravenous catheter apparatus of all embodiments herein disclosed may be secured by ultrasonic welding, solvent bonding, glue, adhesive, and/or other heat or chemical methods known in the art. In at least one aspect of the present disclosure, the housing or its subassemblies is designed such that the welding process will capture the elastomeric member between housings producing the normally-closed seal. Housings components can be configured for snap-fit, gluing, spin welding, solvent welding and the like.

Any part of elastomeric member and/or the slit of the elastomeric member may be lubricated. In one aspect, a silicone lubricant may be used. Different lubricants may be used on different surfaces of the elastomeric member. One or more silicone fluid may be compounded into the elastomeric member during molding.

The housing and/or supports and further components of the intravenous catheter apparatus can be injection-molded out of a rigid, biocompatible, engineering grade resin such as polycarbonate, cyclic olefinic copolymer (COC or transparent acrylonitrile butadiene styrene (MABS), and the like. Certain configurations of the elastomeric member may be constructed using a thermoplastic elastomer TPE, which is likewise injection molded. Liquid injection molding (LIM) can be used for the elastomeric member and/or to create the valve assembly. Compression molding or rotational compression molding can be used to manufacture the elastomeric member. Elastomeric materials can be of silicone, polyurethane for such molding methods.

In regard to the further features of the IV catheter apparatus, the following is to be mentioned:

The disc-like retaining protrusion has the benefit that it is in engagement along a circular contact surface with the corresponding retaining depression formed in the inner surface of the catheter hub. Differing from IV catheter apparatuses as known from the prior art, this provides an engagement between the needle guard and the catheter hub along a substantial annular portion of the retaining protrusion and the retaining depression which provides a safe and reliable engagement between the two components as long as the needle guard is in its ready position and is to be prevented from being retracted out of the needle hub. Even if the needle guard is rotated within the catheter hub, this secure engagement between the catheter hub and the needle guard holds the needle guard safely within the catheter hub.

Because of a depression being formed in the inner surface of the catheter hub for retaining the needle guard in the chamber, instead of e.g. a protrusion, the catheter hub can be manufactured more easily and, thus, at less manufacturing cost, in particular if the catheter hub is a plastic part and e.g. formed by injection molding. At the same time the particular design of the first retaining protrusion provided on the needle guard ensures effective engagement of the retaining protrusion with the retaining depression and, thus, reliable retaining of the needle guard in the catheter hub. Hence, the risk of premature release of the needle guard from the catheter hub during withdrawal of the needle from the catheter hub and, thus, the risk of accidental pricking by the needle is reduced.

According to a preferred embodiment, the retaining protrusion is of part-circular, in particular semi-circular shape. More specifically, the retaining protrusion may have generally parallel proximal and distal faces and/or a convex, in particular part cylindrical, peripheral surface.

According to another embodiment, the first retaining protrusion is arranged in the region of a distal end of the first arm.

According to yet another embodiment, a second disk-like retaining protrusion is arranged on the second arm and adapted to engage with the retaining depression as long as the first arm is in its deflected state.

According to yet another embodiment, the second arm can be deflected, preferably along its entire length, radially inwards when the needle tip is received between the arms, to thereby allow the second retaining protrusion to disengage from the retaining depression.

According to yet another embodiment, the second retaining protrusion is arranged in the region of a distal end of the second arm. In particular, the second retaining protrusion may be arranged opposite from the first retaining protrusion.

According to yet another embodiment, the retaining depression is an at least part annular depression, preferably an annular depression.

According to yet another embodiment, the restoring force is created by at least one of an elastic property of the first arm and a tension element. For example, the needle guard may comprise a tension element at least partly surrounding the arms in a region proximal of the first retaining protrusion or—instead of surrounding the two arms—biasing the two arms by a linear biasing action. Alternatively or additionally, the first and second arms can be made of a resilient material.

According to yet another embodiment, the first and second arms are made of a plastic material. Preferably, the first and second arms are integrally formed with the base portion also made of a plastic material, e.g. by injection molding.

For the purpose of a simplified and cost-effective production of the needle guard, the integrated tension element or resilient member may be formed integrally onto the arms, for example, by injection and/or insert moulding such that the entire needle guard has a unitary structure.

According to yet another embodiment of the present invention the integrated resilient member or elastic element may comprise a ring like integrated form/structure partially or fully surrounding the arms, and/or clamp, bracket, "C" clip or the like surrounding the arms only in part.

Alternatively or additionally, the base portion and the first and second arms may be formed from a metal material or combination of materials, such as a different plastic material, a different metal material or a different combination of plastic and/or metal materials. For example, one of the arms may be made of a metal material and other one may be made of plastic material. Likewise, the base portion may be made from a metal material and the arms may be made from a plastic material or vice versa. It is also to be noted that the inner part of the arms which contacts the needle shaft can be made from a thermoplastic material such as TPE, whereas the outer part of the arms may be made from a different material, for example, a plastic, metal, composite or elastomer material, so that the needle guard causes less friction when sliding along the needle thereby facilitating the withdrawal of the needle.

According to yet another embodiment, the needle comprises an engagement means provided at a distance from the needle tip for engaging with the needle guard and preventing the needle guard from sliding off the needle. Preferably, the engagement means is formed of by enlargement of the radial dimension of the needle in at least one direction as compared with a principal profile of the needle. The engagement means can be found by a local crimp, a shoulder, a bulge formed as an annular widening etc.

According to yet another embodiment, the needle guard comprises a stopping element engaging with the engagement means of the needle when the needle tip is received between the first and second arms. Preferably, the stopping element defines an axial bore having a cross-section adapted to the principal profile of the needle but being smaller than the enlargement of the needle. Furthermore, the stopping element may be made of a material different from the material of the base portion, in particular of a metal material. The stopping element may be of disc-like shape or tubular shape and/or arranged on a distal side of the base portion. It can be fixed in the base portion or supported in a floating manner on the needle.

A preferred embodiment of the invention will now be described by way of example only with reference to the accompanying drawings.

Embodiments of the present disclosure now will be described more fully hereinafter with reference to the accompanying drawings, in which embodiments of the present disclosure are shown. This present disclosure may, however, be embodied in many different forms and should not be construed as limited to the embodiments set forth herein. Rather, these embodiments are provided so that this disclosure will be thorough and complete, and will fully convey the scope of the claims to those skilled in the art. Like numbers refer to like elements throughout.

LISTING OF FIGURES

FIG. 1 is a longitudinal view of an intravenous catheter apparatus according to the present invention;

FIG. 2 is a longitudinal sectional view of the intravenous catheter apparatus of the present invention;

FIG. 3 is a longitudinal sectional view according to FIG. 2 without a needle cover;

FIG. 6 is a perspective explosive view of another embodiment of the intravenous catheter apparatus according to the present invention;

FIG. 7 is a longitudinal sectional view of a needle guard of the intravenous catheter apparatus of FIG. 5 without a tension element;

FIG. 8 is a top view of the needle guard of FIG. 7;

FIG. 11 is a plan view, with sectional plane A-A, of an embodiment of a pressure activated valve in accordance with the present disclosure;

FIG. 12 is a top view of FIG. 11 showing sectional planes 14A-14A and 14B-14B;

Figures 21A, 21B:
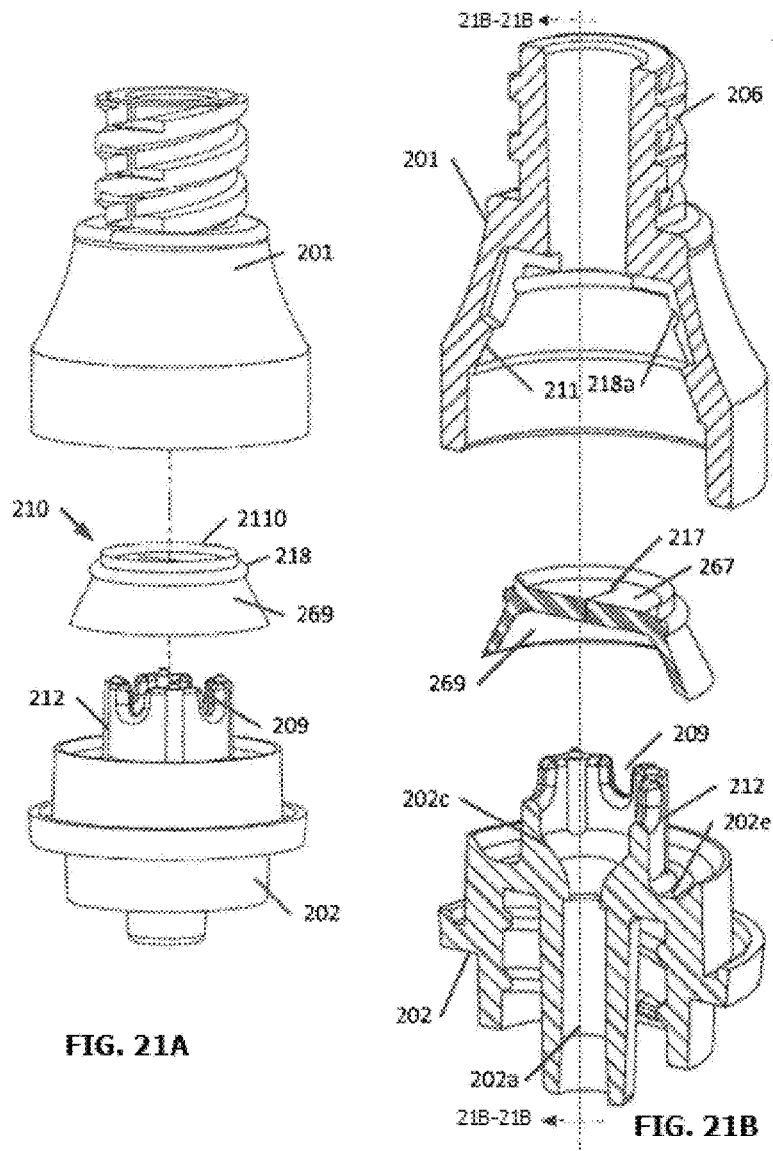
Figure 23A:
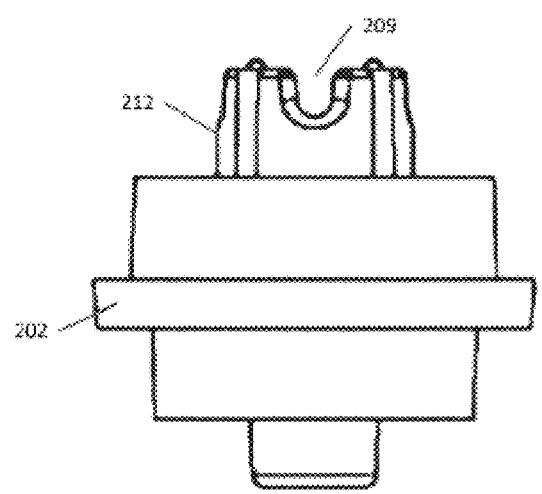
Figure 23B:
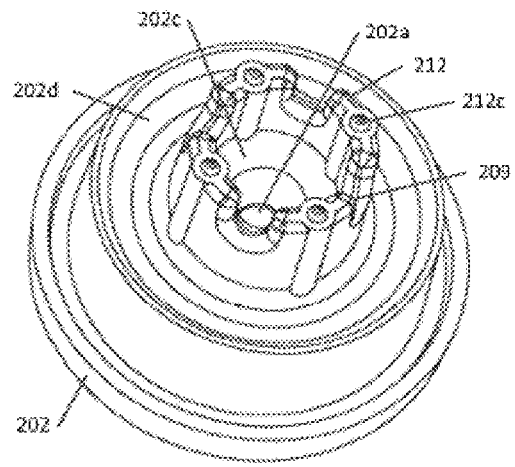
Figures 26A, 26B:
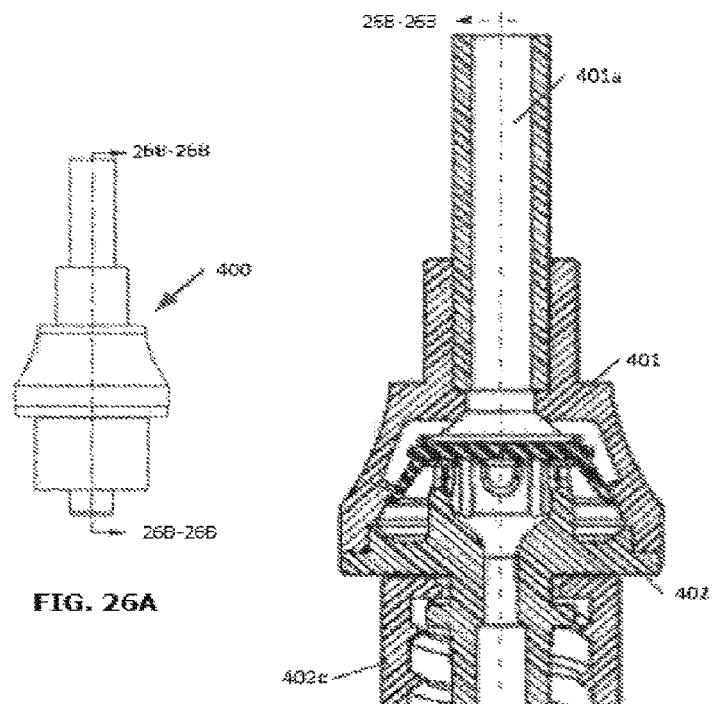
Figures 27A, 27B:
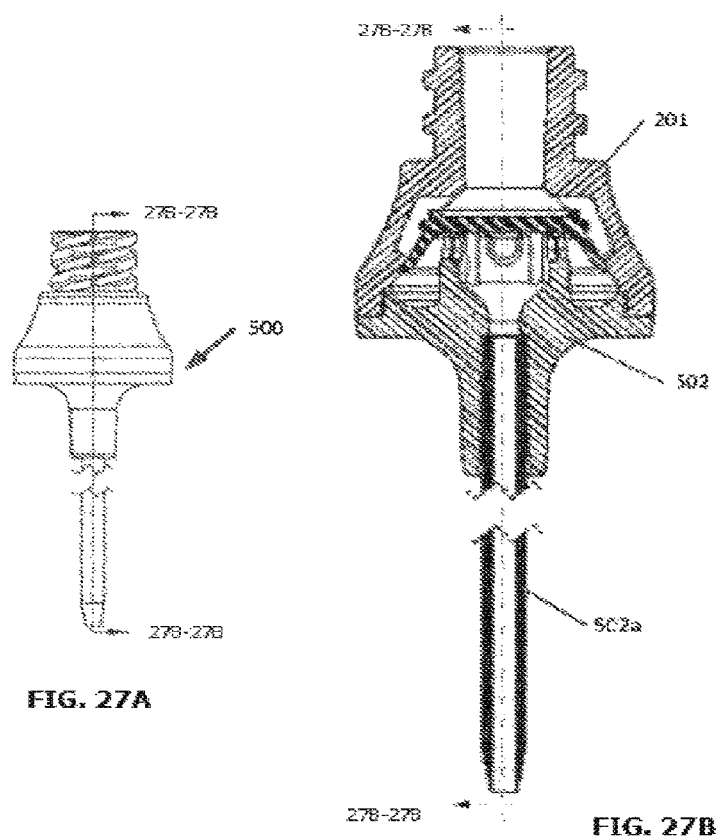
Figures 28A, 28B:
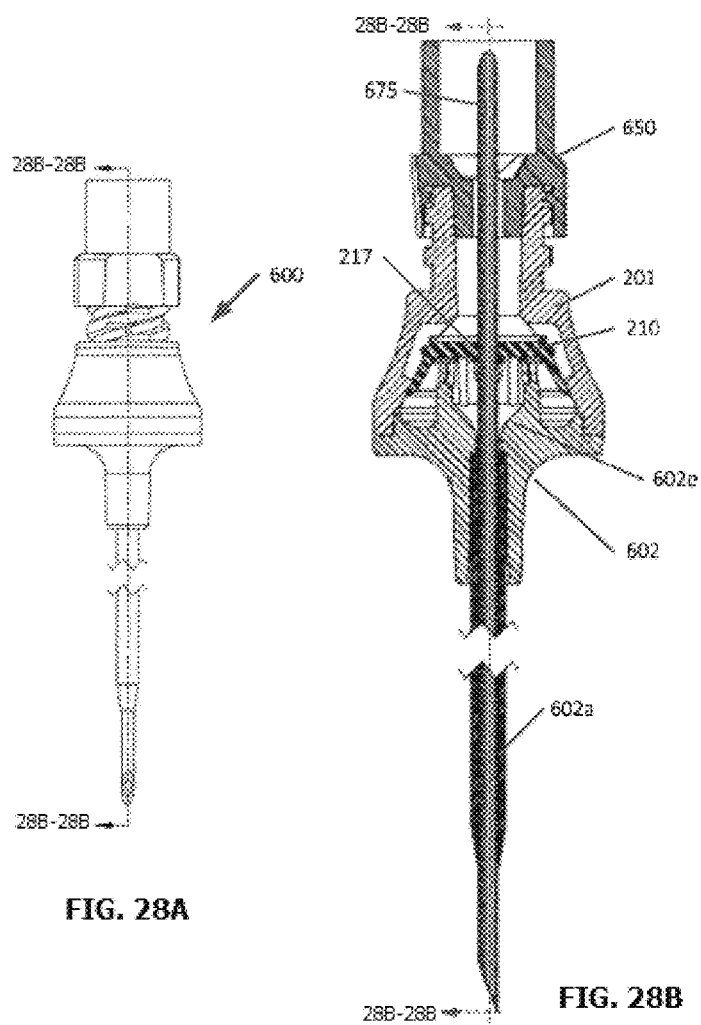
Figure 32A:
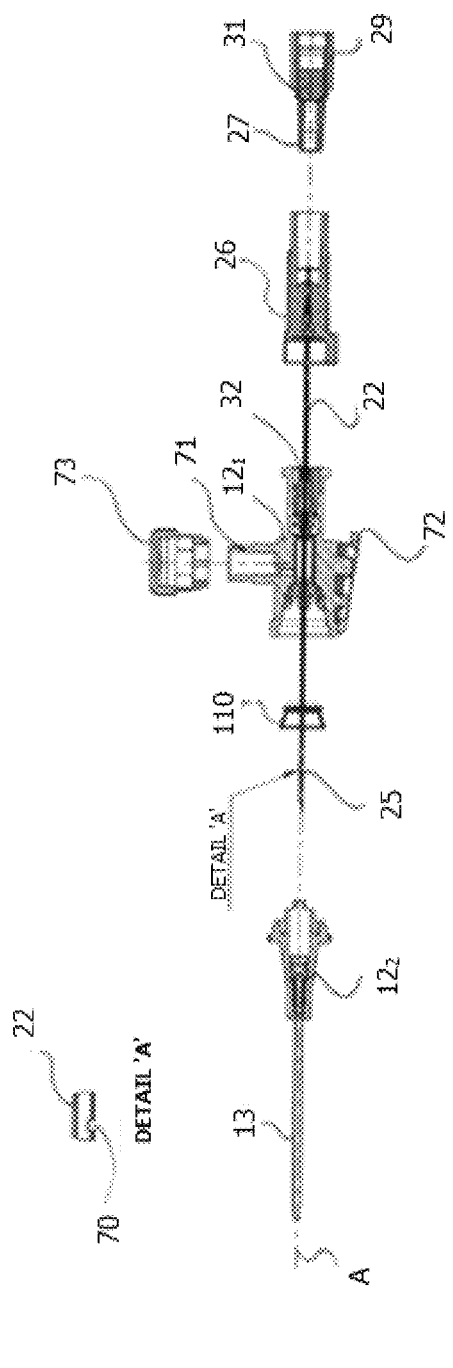
Figure 32B:
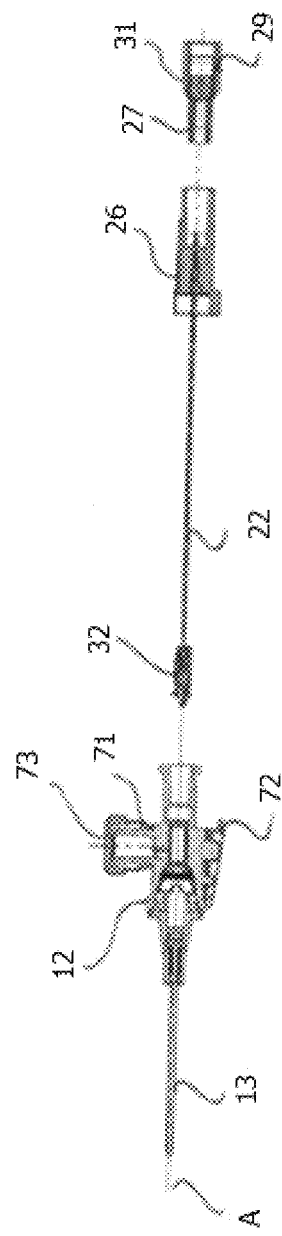

FIGS. 18A, 18B, 18C, and 18D are perspective views of the elastomeric member in accordance with embodiments of the present disclosure;

FIG. 19 is a plan view, with sectional planes B-B, of another embodiment of a pressure activated valve in accordance with the present disclosure;

FIG. 20 is a top view of FIG. 11 showing sectional planes 22A-22A and 22A-22A;

FIGS. 21A and 21B are an exploded view and exploded sectional view, respectively of the embodiment of FIG. 19;

FIG. 22A and FIG. 22B are cross-sectional views of the embodiment of FIG. 19 along sectional planes 22A-22A and 22B-22B, respectively;

FIGS. 23A and 23B are a plan view and a perspective view of the lower housing, respectively, of the embodiment of FIG. 19;

FIG. 24A and FIG. 24B are cross-sectional views of the embodiment of FIG. 19 along sectional planes 22A-22A and 22B-22B, respectively, in a first state of operation and in a second state of operation, respectively;

FIGS. 25A, 25B, and 25C are sectional views of another embodiment of a pressure activated valve in accordance with the present disclosure, FIG. 25B showing the embodiment of FIG. 25A rotated 90°;

FIG. 26A is a plan view, with sectional plane 26B-26B, of another embodiment of a pressure activated valve in accordance with the present disclosure;

FIG. 26B is a cross-sectional view along sectional plane 26B-26B, of the embodiment of FIG. 26A;

FIG. 27A is a plan view, with sectional plane 27B-27B, of another embodiment of a pressure activated valve in accordance with the present disclosure;

FIG. 27B is a cross-sectional view along sectional plane 27B-27B, of the embodiment of FIG. 27A;

FIG. 28A is a plan view, with sectional plane 28B-28B, of another embodiment of a pressure activated valve in accordance with the present disclosure;

FIG. 28B is a cross-sectional view along sectional plane 28B-28B, of the embodiment of FIG. 28A;

FIG. 29A is a plan view, with sectional plane 29B-29B, of another embodiment of a pressure activated valve in accordance with the present disclosure;

FIG. 29B is a cross-sectional view along sectional plane 29B-29B, of the embodiment of FIG. 29A FIG. 30A is a longitudinal sectional view of another embodiment of the present invention;

FIG. 30B shows a detail of the needle close to the needle tip according to the embodiment of FIG. 30A;

FIG. 31A is a longitudinal sectional view of still another embodiment of the present invention; and FIG. 31B shows a detail of the needle close to the needle tip according to the embodiment of FIG. 31A;

FIGS. 32A & 32B are a longitudinal sectional view of still another embodiment of the present invention;

DETAILED DESCRIPTION OF EMBODIMENTS

In accordance with the present invention, an intravenous catheter apparatus which provides better protection against accidental pricking by the needle tip and which is inexpensive to manufacture at the same time is provided is provided. While this invention is susceptible of embodiments in many different forms, there will be described herein specific embodiments with the understanding that the present disclosure is to be considered as an exemplification of the principles of the invention and is not intended to limit the invention to the embodiments detailed herein.

As used herein, the term "proximal" refers to a region of the device or a location on the device which is closest to, for example, a clinician using the device. In contrast to this, the term "distal" refers to a region of the device which is farthest from the clinician, for example, the distal region of a needle will be the region of a needle containing the needle tip which is to be inserted e.g. into a patient's vein.

Prior to the use of the catheter apparatus, the needle guard is arranged in the catheter hub near a proximal end of the needle shaft. In this situation, the needle extends completely through the needle guard, thereby deflecting the first arm of the needle guard outwards, i.e. at an angle to the axial direction, such that the distal wall of the first arm is supported on the needle shaft. Following the insertion of the catheter into a patient, the successful venipuncture is ascertained by the blood visible from the lateral opening provided in the needle. Thereafter, the needle is withdrawn from the catheter tube and the needle shaft moves through the needle guard while the needle guard is retained in the catheter hub. Once the needle tip passes the transverse distal wall of the needle guard, i.e. such that the needle shaft no longer supports the distal wall, a restoring force ensures that the first arm of the needle guard is moved back into alignment with the axial direction of the needle guard, so that the needle tip is blocked by the distal wall of the needle guard, i.e. the needle tip is prevented from axially projecting out of the needle guard.

Once the needle tip is blocked by the distal wall, the enlargement of the needle shaft engages with the stopping element, when the stopping element is arranged between the arms, or with the distal side of the base portion, when the stopping element is arranged in the base portion, to prevent the needle guard from being removed from the needle shaft. The fact that the stopping element is made from a second material which is harder and less easily distorted than the first material of the base portion, has the effect that the needle guard is secured more effectively on the needle shaft and can be retained even if excessive external force is applied when pulling on the needle, as the enlargement is prevented from being pulled through the base portion of the needle guard due to the stopping element. Hence, it is less likely that the needle guard is removed from the needle tip accidentally and, as a result, the needle guard provides a better protection against accidental pricking and thus increased safety for the person handling the catheter apparatus.

FIGS. 1 and 2 show an intravenous catheter apparatus 10 according to the first embodiment of the invention. The intravenous catheter comprises a catheter hub 12 and a catheter tube 13 attached to the catheter hub 12 at a distal end of the catheter hub 12. It will be appreciated that the term 'proximal' refers to a position or orientation close to a person handling the intravenous catheter apparatus whereas the term 'distal' refers to a position or orientation distant from this person, wherein the longitudinal direction A of a needle 20 is the reference direction.

A proximal portion $12_1$ of the catheter hub 12 has an inner surface 14 which defines a chamber 16 of generally circular cross-section. The chamber 16 is located in a proximal section of the catheter hub 12. In a distal region of the chamber 16 the inner surface 14 of the catheter hub is provided with an annular retaining protrusion 18 the function of which will be discussed in more detail further below.

The catheter hub 12 also includes a distal catheter hub portion $12_2$. The proximal catheter hub portion $12_1$ is formed at its distal end with a conical female section 15. The distal catheter hub portion $12_2$ is formed at its proximal and with a conical male section 17. The conical female section 15 and the conical male section 17 are formed with ring-shaped protrusions and recesses which are provided to engage into one another in order to fix the proximal catheter hub portion $12_1$ and the distal catheter hub portion $12_2$ to one another in a snap-fit arrangement. The fixation can be supported by additional adhesive or other ways of fixation, e.g. welding. The conical female section 15 forms an internal hollow space 19, which will be discussed further in regard to a valve arrangement. This valve arrangement includes an elastomeric element 110.

The needle 20 having distal and proximal ends extends through the chamber 16 of the catheter hub 12 as well as through the catheter tube 13. The needle 20 comprises a needle shaft 22 and a needle tip 24 at its distal end. A needle hub 26 is attached to the proximal end of the needle 20. At the proximal end the needle hub 26 has a hollow space which receives a plug 27 having a passage 29 which receives a porous filter element 31.

Figure 4:
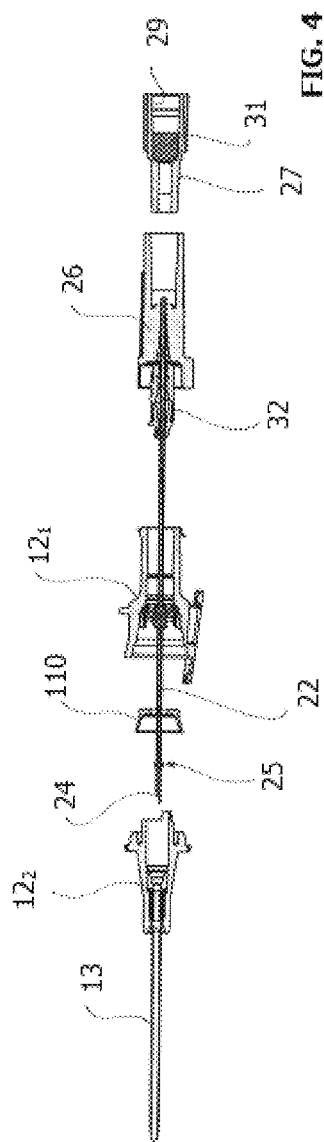
FIG. 4 is an explosive longitudinal sectional view of the intravenous catheter apparatus according to the present invention.

The needle 20 defines said axial (longitudinal) direction A and the needle shaft 22 has a generally constant principal profile, except for an enlargement of the radial dimension of the needle 20 in at least one direction as compared to the principal profile, which is positioned in the region of the needle tip 24 and forms an engagement means, that can be seen in FIG. 4 at reference sign 25. Preferably, the engagement means is made by crimping of the needle 20. However, it could also be made by welding, milling, cold heading or expanding of the needle. The function of the engagement means will be discussed in more detail further below.

FIGS. 1, 2 and 3 show the intravenous catheter apparatus in a condition prior to use. In this condition prior to use the needle 20 extends all the way through the chamber 16 of the catheter hub 12 as well as the catheter tube 13 and the needle tip 24 protrudes from a distal end of the catheter tube 13. This position of the needle 20 is also referred to as the ready position in this context. It is to be noted that the needle 20 is fixed in its ready position by the needle hub 26 engaging with the catheter hub 12.

In order to prevent accidental pricking by the needle 20 prior to use of the intravenous catheter apparatus, a tubular cover 30 covers the catheter tube 13 and the portion of the needle 20 extending therethrough. A proximal end portion of the cover 30 is removably fixed to a distal end portion of the catheter hub 12.

The intravenous catheter apparatus further comprises a needle guard 32 for protecting the needle tip 24 after use of the needle 20, i.e. after placement of the catheter tube 13 in and withdrawal of the needle 20 from a patient's vein. The needle guard 32 is slidably arranged on the needle shaft 22 and received in the chamber 16.

FIG. 4 shows an exploded view with the components described above, which however is not a condition of use. This exploded view rather shows the way, how the IV catheter apparatus according to the invention can be assembled.

Figure 5:
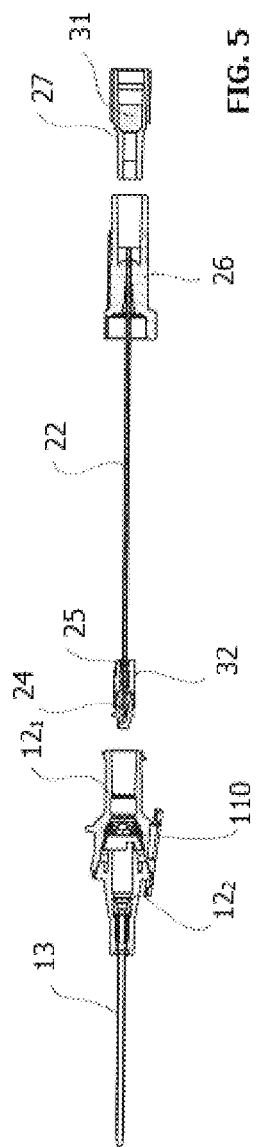
FIG. 5 is a longitudinal sectional view of the intravenous catheter apparatus according to the present invention in the retracted state.
Figure 9:
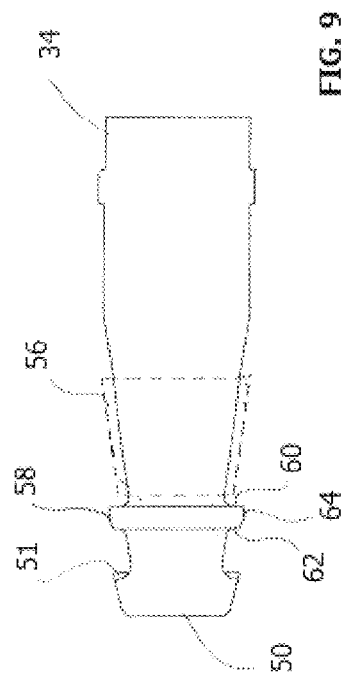
FIG. 9 is a bottom view of the needle guard of FIG. 7.
Figure 10:
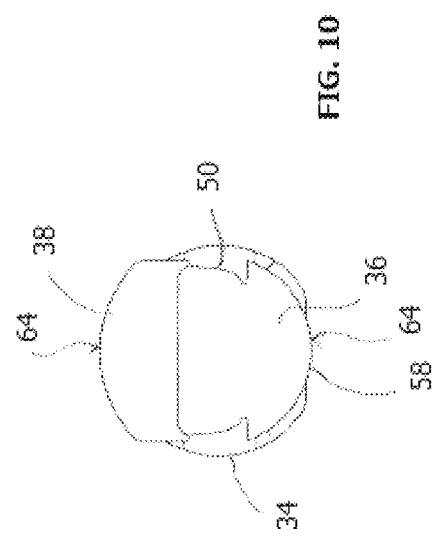
FIG. 10 is a front view of a distal end of the needle guard of FIG. 7.

FIG. 5 shows the IV catheter apparatus according to this embodiment of the invention in a retracted condition when the needle is retracted out of the catheter hub 12. In this condition, the needle tip 24 is covered by the needle guard 32, wherein the needle featured 25 prevents that the needle guard 32 is removed from the needle in distal direction. The needle tip 24 is covered by the needle guard 32. The plug 27 can be removed from the needle hub 26. The catheter tube 13 may be introduced into a patient's vein, which is not shown in detail.

FIG. 6 shows the whole arrangement in a further perspective exploded view. It also shows a hollow fixation plug 31 for fixing the catheter tube 13.

As can be seen in more detail in FIGS. 7 to 10, the needle guard 32 comprises a tubular base portion 34 and first and second arms 36, 38 extending from a distal side of the tubular base portion 34 generally in the axial direction. The base portion 34 and the arms 36, 38 are integrally made of a plastic material, for example by injection molding.

The base portion 34 has an axial through-bore 40 for receiving the needle 20. The throughbore 40 comprises first and second sections 42, 44 both having cross-sections that are larger than the principal profile of the needle 20, the cross-section of the second section 44 being even larger than the cross-section of the first section 42.

A stopping element 46 in the shape of a disk-like plate, such as a washer, is arranged at the distal side of the base portion 34, for example by insert molding. The stopping element 46 is made of a material different from the material of the base portion 34, for example of a metal material. The stopping element 46 has an axial bore 48 which is aligned with the through-bore 40 of the base portion 34 and which has a cross-section which is smaller than that of the through-bore 40 of the base portion 34. More specifically, the cross-section of the axial bore 48 of the stopping element 46 is adapted to the principal profile of the needle 20 such that the stopping element 46 can slide along the needle shaft 22 with minimum friction. However, a maximum dimension of the axial bore 48 transverse to the longitudinal direction A is smaller than a maximum dimension of the engagement means provided on the needle 20 transverse to the longitudinal direction so as to prevent the engagement means from passing through the stopping element 46 and, thus, to prevent the needle guard 32 from sliding off the needle 20.

The first arm 36 of the needle guard 32 is longer than the second arm 38 and has a massive distal end section 50 having an undercut 51 for catching the needle tip 24. The distal end section 50 is angled towards the second arm 38 and overlaps with the second arm 38 (FIG. 8). In its ready position the needle 20 extends completely through the needle guard 32 (FIG. 7). In this situation the distal end section 50 of the first arm 38 is supported on the needle shaft 22 thereby deflecting the first arm 36 radially outwards. In order to facilitate deflection of the first arm 36, the first arm 36 has a narrowed portion 52 of reduced cross-section approximately in a middle region of the arm 36. In contrast to the first arm 36 and because of a lack of angled distal end section, the second arm 38 is not significantly deflected by the needle 20 extending through the needle guard 32. Nonetheless, the second arm 38 has a similar narrowed portion 54 the reason for which will become apparent further below.

Even though the first and second arms 36, 38 have certain elastic properties, a tension element, for example a rubber band 56 (indicated by dotted lines in FIGS. 8 and 9), surrounds a distal section of the arms 36, 38 such that deflection of the first arm 36 occurs mainly against a restoring force of the tension element (FIG. 7).

When the needle 20 is withdrawn from the catheter tube 13 after placement of the catheter tube 13 in a patient's vein, the needle 20 slides through the needle guard 32 until the needle tip 24 passes the angled distal end section 50 of the first arm 36. At this point the angled distal end section 50 is no longer supported on the needle shaft 22 and the first arm 36—mainly by force of its own elasticity supported by the rubber band 56—snaps back into its relaxed state with the angled distal end section 50 now blocking the needle tip 24. It will be appreciated that the length of the first arm 36 and the distance of the engagement means from the needle tip 24 are adapted to each other such that the needle tip 24 received in the needle guard 32 has a minimum of clearance with respect to axial movement in the needle guard 32.

In order to prevent the needle guard 32 from being prematurely removed from the chamber 16 of the catheter hub 12, i.e. before the needle tip 24 is covered by the needle guard 32, the first arm 36 is provided with a disc-like first retaining protrusion 58 engaging with the retaining depression 18 in the inner surface 14 of the catheter hub 14 in the deflected state of the first arm 36. The first retaining protrusion 58 has generally flat proximal and distal faces 60, 62 and a convex, in particular part-cylindrical, peripheral surface 64 the radius of which is adapted to the radius of the inner surface 14 of the catheter hub 12 in the region of the retaining depression 18. The height of the first retaining protrusion 58, i.e. its dimension seen in the radial direction, is adapted such that the first retaining protrusion 58 disengages from the retaining depression 18 when the first arm 36 snaps back into its relaxed state.

The second arm 38 is provided with a disc-like second retaining protrusion 66 which is similar to the first retaining protrusion 58 and which extends in a radial direction opposite from the first retaining protrusion 58. The second retaining protrusion 66 also has generally parallel proximal and distal faces 60, 62 as well as a convex, in particular part-cylindrical, peripheral surface 64. The height of the second retaining protrusion 66, i.e. its dimension seen in the radial direction, is adapted such that the retaining protrusion 66 engages with the retaining depression 18 when the needle 20 is in its ready position. In order to disengage the retaining protrusion 66 from the retaining depression 18, the second arm 38 can be deflected slightly radially inwards towards the needle 20 when the pulling force on the needle 20 becomes great enough.

As can be seen from FIG. 1, the axial dimension, i.e. width, of the retaining depression 18 is significantly larger than the axial dimension, i.e. width, of the retaining protrusions 58, 66. For example, the width of the retaining depression 18 can be three to five times the width of the retaining protrusions 58, 66, although other ratios are possible as long as reliable engagement between the retaining depression 18 and the retaining protrusions 58, 66 is ensured.

As mentioned above, the IV catheter device also includes a valve. In order to explain the structure and the function of the valve, reference is made to the FIGS. 11 to 29B for different embodiments of the valve, which can be integrated into an IV catheter. The valve can be formed separately as discussed in the following or integrated in the catheter device. Therefore, the valve is described separately as device 100. As shown above, the valve can be integrated into the catheter hub 12 which then forms the housing of the valve with at least two catheter hub portions 12₁ and 12₂.

Referring now to the Figures, FIG. 11 is a perspective view of a first embodiment depicting device 100 which forms the valve as a separate component. Device 100 comprises a rigid upper housing 101 for providing connection to a male Luer fitting, and a rigid lower housing 102, which provides for connection to a female Luer fitting. The device has a smooth exterior for patient comfort. Device 100 has a first opening 101a and a second opening 102a. While first opening 101a is shown as threaded, it can be configured smooth without threads. FIG. 12 is top view of device 100 showing sectional planes described further below.

Figure 13:
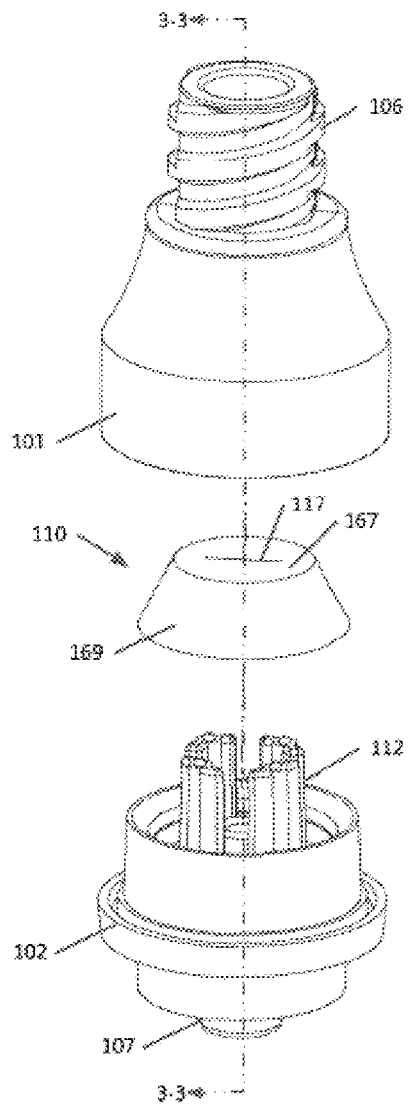
FIG. 13 is an exploded view of the embodiment of FIG. 11.
Figure 14:
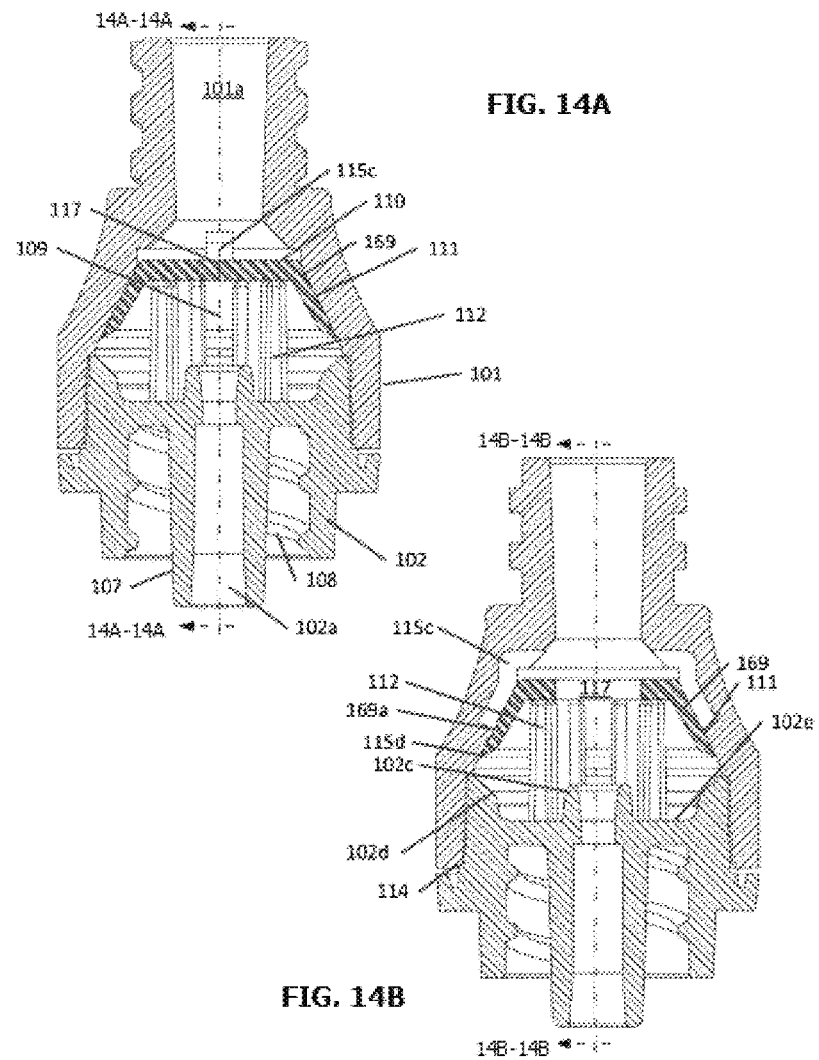
FIG. 14A and FIG. 14B are cross-sectional views of the embodiment of FIG. 11 along sectional planes 14A-14A and 14B-14B, respectively.

FIG. 13 is an exploded perspective view of device 100 depicting lower housing 102, having supports 112, elastomeric member 110 having peripheral wall 169 projecting from surface 167 towards lower housing 102. On surface 167 is slit 117. Upper housing 101 is configured to form fluid tight seal with lower housing 102. Upper housing 101 can be configured with threaded female Luer fittings 106, as shown. The lower housing can be configured with male luer 107 and surrounding internal threads 108, as shown.

Referring now to FIGS. 14A and 14B, cross-sectional views, 90° apart respectively, of first embodiment device 100 in an assembled configuration are shown.

FIG. 14A depicts a portion of peripheral wall 169 of elastomeric member 110 having an interference fit with the interior wall 111 forming a continuous seal with the interior wall 111 of upper housing 101. Elastomeric member 110 partitions device 100 into an upper section corresponding to first opening 101a and lower section corresponding to second opening 102a. Elastomeric member 110 is shown supported by supports 112. Supports 112 form opening 109 and provide fluid communication between lower housing 102 and through second opening 102a. Elastomeric member 110 is shown here as a normally-closed valve, as both slit 117 and continuous seal with interior wall 111 prevent fluid flow between openings 101a and 102a prior to activation of device 100 via a pressure differential. The interference fit between elastomeric member 110 and interior wall 111 of the housing can be provided upon securing upper housing 101 and lower housing 102 during manufacturing e.g., upon bonding/welding the housings components together, for example at weld joint 114. The elastomeric member is supported by supports 112 and the elastomeric member is sealed against the interior wall 111 of the upper housing. Fluid is able to flow between the supports into opening 109 and through first opening 101a. Lower housing 102 includes base 102e surrounding projection 102c which projects from base 102e as part of second opening 102a. Surface (or base) 102e extends radially outward to tapered wall 102d. A portion of the outer diameter of tapered wall 102d is configured for sealable arrangement via weld joint 114 with an interior diameter of upper housing 101.

FIG. 14B depicts an aspect of the first embodiment whereby fluid channel 115c is provided in interior wall 111 of upper housing 101. As shown, fluid channel 115c extends generally parallel to the longitudinal axis of device 100 towards lower housing 102. The distal terminus of the length of fluid channel 115c (e.g., distal end 115d) is configured to be such that at least a portion of peripheral wall 169 (e.g., as shown, distal end 169a) remains continuously in interference with interior wall 111. In one embodiment, device 100 can be configured without fluid channel 115c (width equal 0).

In one aspect, two or more fluid channels 115c are provided in interior wall 111 of upper housing 101. In such an aspect, two fluid channels 115c can be arranged in a parallel configuration with both their corresponding longitudinal axes substantially aligned with the longitudinal axis of device 100. In one embodiment, elastomeric member has slit 117 formed of a single slit, and the two fluid channels 115c are arranged to be orthogonal with the longitudinal axis of the single slit 117. In this configuration, during infusion of fluid, and upon deflection of peripheral wall 169, radial forces are applied to surface 167 to facilitate maintaining closure of slit 117.

Figure 15:
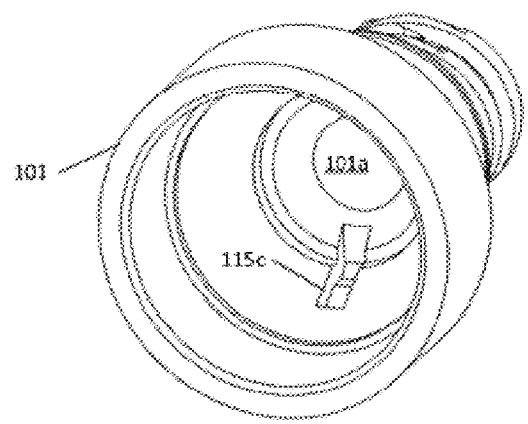
FIG. 15 is a perspective view of the upper housing of the embodiment of FIG. 11.
Figure 16:
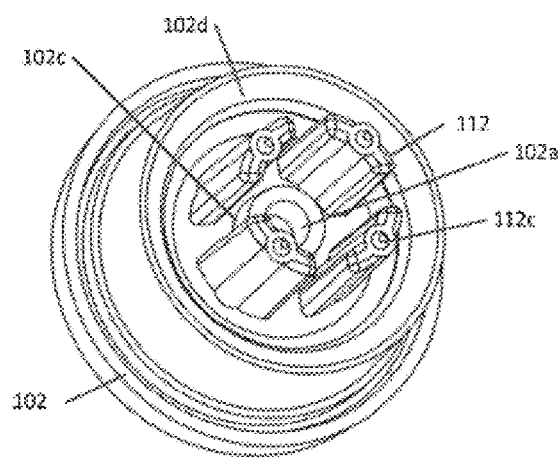
FIG. 16 is a perspective view of the lower housing of the embodiment of FIG. 11.

FIG. 15 shows a perspective view of upper housing 101 depicting fluid channel 115c, as shown, in fluid communication with first opening 101a and having a length generally parallel with the longitudinal axis of upper housing 101. The width of fluid channel 115c can be chosen to be approximately any width equal to a number greater than zero and less than of one half the maximum internal perimeter length of upper housing 101. In one aspect, fluid channel 115c width is chosen to be less than the minimum internal diameter of first opening 101a so as to facilitate a focused pressure or force (and/or accelerated fluid velocity) on peripheral wall 169 during infusion and/or flushing of device 100. FIG. 16 shows a perspective view of lower housing 102 depicting a plurality of supports 112 arranged about projection 102c of second opening 102a. Supports 112 are arranged radially around projection 102c with spacing therebetween so as to allow fluid communication between the upper housing 101 first opening 101a and lower housing 102 second opening 102a during infusion. Supports 112 can have distal projections 112c configured to contact lower surface of elastomeric member 110 and to minimize shifting of the elastomeric member 110 within the housing during assembly or use and/or to apply a preload and/or to account for the stack up of the upper and lower housing components.

Figures 17A, 17B:
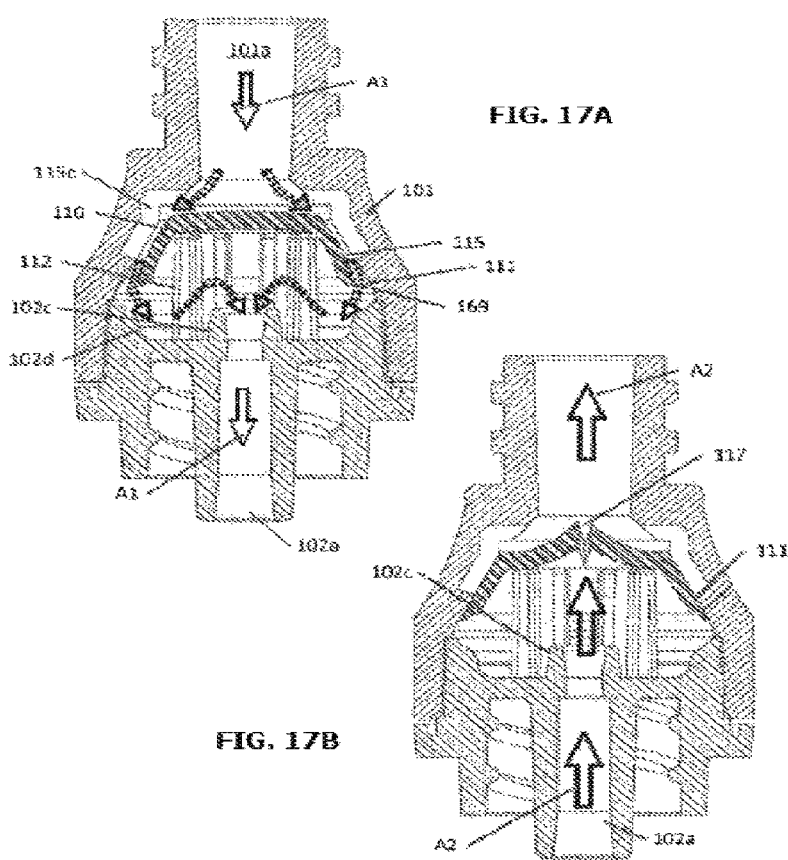
FIG. 17A and FIG. 17B are cross-sectional views of the embodiment of FIG. 11 along sectional planes 14A-14A and 14B-14B, respectively, in a first state of operation and in a second state of operation, respectively.

FIGS. 17A and 17B are cross-sectional views of device 100 shown in a first state (e.g., infusion) and a second state (e.g., aspiration), respectively. Arrows A1 and A2 depict fluid flow direction within device 100.

With reference to FIG. 17A, in a first state, a pressure differential between the partitioned housing is created upon infusion of fluid through first opening 101a that causes deflection of peripheral wall 169 from interior wall 111 of upper housing 101 creating fluid passage 115 and allowing fluid communication between the upper portion and lower portion of device 100 around elastomeric member 110, while maintaining closure of slit 117, so as to provide directional fluid flow from first opening 101a through second opening 102a. Structures of lower housing 102, e.g., tapered wall 102d and projection 102c, can provide turbulence and/or fluid flow direction so as to enable effective flushing of elastomeric member portions that have been contacted with bodily fluids (e.g., the interior surface of peripheral wall 169). Peripheral wall 169, which in various aspects, provides an oval, cup-like, or conical frustum-shaped (or frustoconical), is configured to deflect and/or flex inward towards the central longitudinal axis of device 100 upon creating a differential in pressure, (for example through the introduction of infusion fluid the opening 101a) with a relatively low infusion cracking pressure threshold. A relatively low infusion cracking pressure threshold is that of approximately 6 to about 36 inches H20 (0.2 psig to about 1.3 psig; where the term "about" encompasses±20% of the stated value). Such pressures are obtained, for example, when an IV bag is raised above the height of an insertion point in a patient. Unlike existing valves that flow "through" an elastomer seal/valve in both an infusion state and an aspiration state, the presently disclosed valve is configured to flow "around" the valve in an infusion state and through the valve in an aspiration state. The advantage of this present configuration is that leaking and "reflux" after aspiration is all but eliminated and the desirable ability to easily infuse fluid via gravity is provided as described with reference to the exemplary embodiment of FIGS. 17A and 17B.

With reference to FIG. 17B, in a second state, a pressure differential created upon aspiration of fluid through the second opening 102a causes slit 117 to open whereas distal end 169a of peripheral wall 169 is maintained in continuous sealable interference contact with interior wall 111 of upper housing 101. In one aspect, the slit is configured such that an aspiration pressure threshold is required to allow fluid to pass through the slit from second opening 102a through first opening 101a. In one aspect, the aspiration pressure threshold is considerably higher than that of the infusion cracking pressure threshold. In one aspect the difference between the aspiration pressure threshold and that of the infusion aspiration threshold is such that the aspiration threshold cracking pressure is approximately 5 psig greater than that of the infusion threshold cracking pressure. This difference in threshold cracking pressure can range between about 3 psig and about 7 psig, (where "about" encompasses±20% of the value). Configuring the difference in threshold cracking pressures can be accomplished by varying the elastic modulus, thickness and/or thickness variation, taper, cross-linking/cure, and material selection and dimensions of elastomeric member 110 as well as the design and arrangement of slit 117, discussed further below. Additional parameters that can be adjusted with regard to cracking pressure thresholds include the number, width, and length of flow channel 115c and/or internal geometries of upper and lower housing components.

Figure 18A:
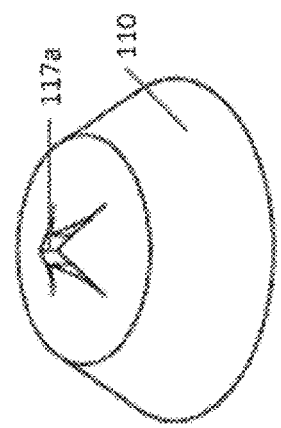
Figure 18B:
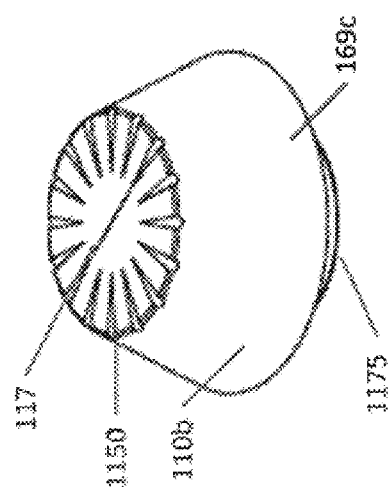

With reference to FIGS. 18A, 18B, 18C, and 18D, variations of the elastomeric member are shown. FIGS. 18A and 18B, depict elastomeric member 110 having a single slit 117 and multislit 117a configuration. Other slit configurations can be used.

Figure 18C:
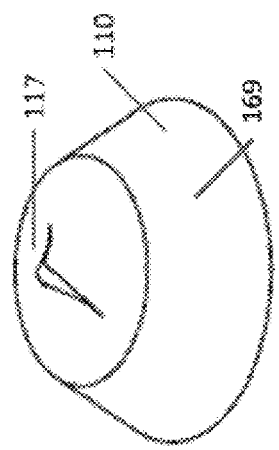
Figure 18D:
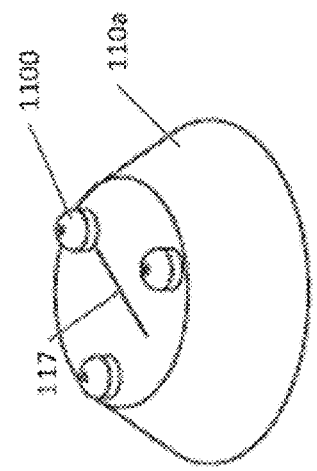

FIGS. 18C and 18D depict modified elastomeric members 110a and 110b, respectively, having additional features on the exemplary conical frustum-shaped member 110a, 110b, namely projections 1100 on surface of conical frustum-shaped member 110a, or one or more channels 1150 in the surface of conical frustum-shaped member 110b.

FIG. 18D further depicts an embodiment of the elastomeric member where in the conical frustum-shaped member 110b includes a stem 1175 with a conduit (not shown) there through surrounded by peripheral wall 169c, the conduit configured to surround second opening 102a or securely surround projection 102c of lower housing 101. Stem 1175 can be configured as a conduit for fluid communication with opening 102a and slit 117. In this configuration, stem 1175 necessarily comprises one or more vertically arranged (with housing longitudinal axis) openings/slits there through (not shown) for fluid passage/flushing during infusion, the opening/slits can be configured to respond to a compressive infusion pressure/force and at least to partially open allowing fluid to enter opening 102a, whereas, during aspiration, the openings/slits, not subject to the compressive stress, would remain closed to facilitate substantially all fluid flow thru opening 102a, stem 1175, slit 117, upper section of housing and opening 101a. In this modification of the elastomeric member embodiment described above, all other functional attributes, as described above for elastomeric member 110, would be maintained.

With reference to FIG. 19, a second embodiment of the presently disclosed valve is shown, depicting a perspective view of device 200, having upper housing 201 with first opening 201a and lower housing 202.

FIG. 20 depicts a top view of device 200 with sectional planes 22A-22A and 22B-22B.

FIGS. 21A and 21B depict an exploded view an exploded sectional view, respectively, of device 200. Lower housing 202 of device 200 includes annular wall 212. In this exemplary embodiment, annular wall 212 provides support to elastomeric member 210, which is surrounded by peripheral wall 269. Annular wall 212 can be integral with lower housing 201 as shown, or can be molded separately and arranged in housing during assembly. Elastomeric member 210 has lateral annular protrusion 218 from edge of surface 267 configured to be received by recess 218a within interior wall 211 of upper housing 201. In addition, elastomeric member 210 includes vertical annular projection 2110 from surface 267 for providing interference upon assembly of upper and lower housing components 201, 202. Surface 267 of elastomeric member 210 includes slit 217, which passes through the thickness of surface 267. Differing from the previous embodiment, lower housing 202 of device 200 includes tapered opening 202c feeding into second opening 202a. Tapered opening 202c provides guidance for insertion of medical devices such as guide wires, etc. into smaller diameter second opening 202a and prevents kinking and/or bending of such devices.

Referring now to FIGS. 22A and 22B, cross-sectional views, 90° apart, respectively, of second embodiment device 200 in an assembled configuration are shown. FIG. 12A depicts a portion of peripheral wall 269 of elastomeric member 210 having an interference fit with the interior wall 211 forming a continuous seal with the interior wall 211 of upper housing 201. Elastomeric member 210 partitions device 200 into an upper section corresponding to first opening 201a and lower section corresponding to second opening 202a. Elastomeric member 210 is shown supported by annular projection 212 that includes flow passages 209 that provide fluid communication between lower housing 202 and through second opening 202a. Elastomeric member 210 is shown here as a normally-closed valve, as both slit 217 and continuous seal with interior wall 211 prevent fluid flow between openings 201a and 202a prior to activation of device 200 via a pressure differential. The interference fit between elastomeric member 210 and interior housing wall 211 can be provided upon securing upper housing 201 and lower housing 202 during manufacturing e.g., upon bonding/welding the housings components together, for example at weld joint 214. The peripheral wall 269 of elastomeric member 210 forms a fluid-type seal with interior wall 211. Fluid is able to flow through annular support 212 at openings 209 and second opening 202a. Lower housing 202 includes surface or base 202e surrounding annular support 212 which projects from base 202e as part of second opening 202a. Surface or base 202e extends radially outward to tapered wall 202d. A portion of the outer diameter of tapered wall 202d is configured for sealable arrangement via weld joint 214 with an interior diameter of upper housing 201. FIG. 22B depicts an aspect of the second embodiment whereby interior diameter of annular support 212 tapers inwardly to that of internal diameter of second opening 202a which also serves as guiding means for medical devices that may be inserted through the device.

In a manner similar to that of the first embodiment, device 200 comprises optional fluid channel 215c that extends generally parallel to the longitudinal axis of device 200 towards lower housing 202. In one embodiment, any of the devices herein disclosed can be configured without fluid channel 215c.

FIG. 23A shows a side view of lower housing 202 depicting annular support 212 and passage 209. FIG. 23B is a perspective view of lower housing 202 showing annular support 212 and tapered opening 202f feeding into second opening 202a. Annular support 212 can have distal projections 212c configured to contact lower surface of elastomeric member 210 and to minimize shifting of the elastomeric member 210 within the housing during assembly or use.

Device 200 functions similarly as that of the first embodiment, as depicted in FIGS. 24A and 24B, which show cross-sectional views of device 200 shown in a first state (e.g., infusion) and a second state (e.g., aspiration), respectively. Arrows B1 and B2 depict fluid flow direction within device 200. With reference to FIG. 24A, in a first state, a pressure differential is created between the partitioned housing of device 200 upon infusion of fluid through first opening 201a that causes deflection of peripheral wall 269 from interior wall 211 of upper housing 201 creating fluid passage 215 and allowing fluid communication between the upper portion and lower portion of device 200 around elastomeric member 210, while maintaining closure of slit 217, so as to provide directional fluid flow from first opening 201a through second opening 202a. Structures of lower housing 202, e.g., tapered wall 202d can provide turbulence and/or fluid flow direction so as to enable effective flushing of elastomeric member portions that have been contacted with bodily fluids (e.g., the interior surface of peripheral wall 269). Peripheral wall 269 is configured to deflect and/or flex inward towards the central longitudinal axis of device 200 upon creating a differential in pressure, (for example through the introduction of infusion fluid the opening 201a) with a relatively low infusion cracking pressure threshold as previously described for the first embodiment. With reference to FIG. 24B, in a second state, a pressure differential in the partitioned housing is created upon aspiration of fluid through the second opening 202a that causes slit 217 to open whereas distal edge 269a of peripheral wall 269 is maintained in continuous sealable interference contact with interior wall 211 of upper housing 201. In one aspect, the slit is configured such that an aspiration pressure threshold is required to allow fluid to pass through the slit from second opening 202a through first opening 201a.

FIGS. 25A and 25B depict a third embodiment device 300 shown configured with upper housing 201 and elastomeric member 210 from the second embodiment device 200, whereas annular support 312 having opening 309 is configured so as not to contact the lower surface of elastomeric member 210. Support of elastomeric member 210 is provided solely by lateral annular protrusion 218 and interference with recess 218a as discussed above. FIG. 15C depicts device 333, which has a modification to the lower housing component of device 300, where annular support 312 is completely absent, and surface or base 302e of lower housing 302' has opening 302c to feed into second opening 302a.

FIGS. 26A and 26B are a perspective view and cross-sectional view along sectional plane 26B-26B of a fourth embodiment device 400 showing implementation of the pressure activated valve with a male luer lock housing assembly. Tubing 401a is bonded to tube housing 401, which is joined to male luer housing 402. Male luer lock hub 402c is snap fit to lower housing 402. The function and operation of device 400 is that as similarly described for the previously described embodiments.

FIGS. 27A and 27B are a perspective view and cross-sectional view along sectional plane 27B-27B, respectively, of a fifth embodiment, device 500 assembled with upper housing 201. Device 500 demonstrates how pressure activated valve can be integrated directly into a vascular catheter hub 502. Catheter 502a can be a peripheral IV catheter, a PICC, a CVC, or the like. As shown above and discussed in regard to FIGS. 1 to 9, the IV catheter according to the present invention is additionally provided with a needle guard for preventing accidental needle pricking.

FIGS. 28A and 28B are a perspective view and cross-sectional view along sectional plane 28B-28B, respectively, of a fifth embodiment, device 600 assembled with upper housing 201 and further coupled with male Luer device 650. Device 600 demonstrates how slit 217 of elastomeric member 210 can accommodate medical device 675 inserted through catheter 602a, guided by tapered internal conduit 602e.

FIGS. 29A and 29B are a perspective view and cross-sectional view along sectional plane 29B-29B, respectively, of a sixth embodiment, device 700. Device 700 demonstrates the pressure activated valve of the present disclosure integrated directly with luer-activated valve 701. The pressure activated valve assembly is joined to the luer activated valve assembly at 727. Luer activated valve 701 is assembled into female luer housing 703 and is sealed within it at 728. Device 700 comprising Luer activated valve as shown is an example of one valve, however the pressure activated valve assembly can be integrated with any number of luer activated valves to provide for the benefits as disclosed herein.

FIGS. 30A and 30B, 31A and 31B show another embodiment according to the invention in an explosive view similar to the view according to FIG. 4. The difference is that the needle includes slightly proximal from the needle feature 25 a through-hole formed as a slit 70. The slit 70 extends in transverse direction to the longitudinal axis A of the needle. The slit 70 provides a flashback feature as described in the introductory part of the description.

It is to be added that in regard to the present invention of different embodiments of a safety IV catheter having a needle guard 32 as well a pressure activated valve according to the description of the valve device with reference to FIGS. 11 to 29, the upper housing 101, 201, 701 can be formed by the proximal catheter hub portion $12_1$ and the lower housing 102, 202, 302, 402, 502, 602, can be formed by the distal catheter hub portion $12_2$. It is also possible to combine a separate valve device as described e.g. in regard to FIG. 11 with the safety IV catheter, which is still covered by the invention.

FIGS. 32A and 32B show yet another embodiment of the invention. The difference is that a port 71 extends from the main body of the catheter hub $12_1$ in a direction generally perpendicular to the axial direction A. A cap 73 is provided to cover the port 71. Wings 72 are provided at the main body opposite from the port 71.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated' listed items.

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise.

It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof Unless otherwise defined, all terms (including technical and scientific terms) used herein have the same meaning as commonly understood by one of ordinary skill in the art to which this present disclosure belongs. It will be further understood that terms used herein should be interpreted as having a meaning that is consistent with their meaning in the context of this specification and the relevant art and will not be interpreted in an idealized or overly formal sense unless expressly so defined herein.

Unless otherwise expressly stated, comparative, quantitative terms such as "less" and "greater", are intended to encompass the concept of equality. As an example, "less" can mean not only "less" in the strictest mathematical sense, but also, "less than or equal to." The term "fluid" as used herein refers to a liquid, gas, or combination thereof.

The invention claimed is:

1. A valve comprising:
  a housing having a first opening and a second opening;
  an elastomeric member positioned in the housing, the elastomeric member comprising a continuous peripheral wall projecting from a surface of the elastomeric member; and
  a slit extending through the surface, wherein a continuous portion of the peripheral wall creates a continuous sealable contact with the housing and partitions the housing into an upper section and a lower section, the elastomeric member configured such that upon creating a pressure differential between the upper section and the lower section of the housing causes:
    (i) the peripheral wall to deflect from the housing permitting fluid flow around the elastomeric member; or
    (ii) the slit to open permitting fluid flow through the elastomeric member;
  wherein, an outer diameter of the peripheral wall and/or of the surface it projects from is greater than a corresponding inner diameter of a corresponding mating portion of the housing, and wherein the valve is configured to maintain an interference fit between at least a portion of the elastomeric member and at least a portion of the housing.

2. The valve of claim 1, further comprising a support member positioned in the housing and surrounded by the peripheral wall, the support member configured to provide fluid communication between the first opening and the second opening.

3. The valve of claim 2, wherein the support member is received by or integral with the housing.

4. The valve of claim 2, wherein the support member comprises a plurality of spaced apart columns arranged about the second opening, the distal ends of the plurality of columns surrounded by the peripheral wall.

5. The valve of claim 2, wherein the support member comprises an annular wall arranged around the second opening, the annular wall having at least one fluid flow passage providing fluid communication between the lower section and the second opening.

6. The valve of claim 1, wherein the second opening comprises a conduit that extends into the housing and is surrounded by the peripheral wall.

7. The valve of claim 6, wherein a portion of the conduit extending into the housing is of a larger internal diameter than the conduit extending external to the housing.

8. The valve of claim 1, wherein a portion of the housing is tapered and a distal portion of the peripheral wall tapers in sealable contact therewith.

9. The valve of claim 8, wherein a taper angle of the peripheral wall is greater than a taper angle of a tapered portion of the housing.

10. The valve of claim 1, wherein the upper portion of the housing comprises an interior wall, the interior wall comprising at least one recessed channel therein and extending substantially along the longitudinal axis of the housing, wherein deflection of the peripheral wall from the housing substantially corresponds to a placement of the at least one recessed channel.

11. The valve of claim 1, wherein the surface comprises a top surface and a bottom surface separated from the top surface by a first thickness; and the peripheral wall has a second thickness, and the peripheral wall projects from the bottom surface, wherein the second thickness is less than the first thickness.

12. The valve of claim 1, wherein the elastomeric member further comprises a continuous lateral protrusion along a peripheral edge of the surface, and the housing is configured with a corresponding recess to receive the continuous lateral protrusion and to provide a radial stress to the surface of the elastomeric member.

13. The valve of claim 1, wherein the elastomeric member further comprises one or more vertical protrusions on the top surface, the housing being configured to provide a normal stress to the one or more vertical protrusions.

14. The valve of claim 1, wherein the elastomeric member is concave, convex, or concave and convex on opposing sides of its thickness.

15. The valve of claim 1, wherein the top surface of the elastomeric member has one or more fluid channels terminating at a peripheral edge of the top surface.

16. The valve of claim 15, wherein the peripheral wall deflects from the housing permitting fluid flow around the elastomeric member, wherein the slit of the elastomeric member is formed by a single slit; and the fluid channels are arranged to be orthogonal with a longitudinal axis of the single slit.

17. The valve of claim 1, wherein the elastomeric member is annular, oval, cylindrical, hemispherical, cup-shaped or conical frustum-shaped.

18. The valve of claim 1, wherein the slit opens at a threshold pressure greater than a threshold pressure required to deflect the peripheral wall from the housing.

19. The valve of claim 1, wherein the slit, in combination with the first opening and the second opening, is configured to receive a needle through the housing.

20. The valve of claim 1, wherein the support is configured to receive and/or guide the needle through the housing.

21. The valve of claim 1, wherein the support in combination with the slit is configured to receive and/or guide the needle through the housing.

22. A method of allowing low pressure passage of liquid in one direction through a device, the method comprising:
providing a device comprising a valve, the valve comprising:
a housing having a first opening and a second opening; and
an elastomeric member positioned in the housing, the elastomeric member comprising a continuous peripheral wall projecting from a surface of the elastomeric member; and
a slit extending through the surface, wherein a continuous portion of the peripheral wall creates a continuous sealable contact with the housing and partitions the housing into an upper section and a lower section, the elastomeric member configured such that upon creating a pressure differential between the upper section and the lower section of the housing causes:
(i) the peripheral wall to deflect from the housing permitting fluid flow around the elastomeric member; or
(ii) the slit to open permitting fluid flow through the elastomeric member;
wherein, an outer diameter of the peripheral wall and/or of the surface it projects from is greater than a corresponding inner diameter of a corresponding mating portion of the housing, and wherein the valve is configured to maintain an interference fit between at least a portion of the elastomeric member and at least a portion of the housing;
forming in the device comprising the valve, the interference fit between at least a portion of the elastomeric member and at least a portion of the housing;
creating a pressure differential between the upper section and the lower section of the housing;
causing the peripheral wall to deflect from the housing and permitting fluid flow around the elastomeric member; or
causing the slit to open permitting fluid aspiration through the elastomeric member;
wherein fluid flow direction through the device is controlled, and wherein the interference fit provides low pressure passage of liquid in one direction.

23. The method of claim 22, wherein the elastomeric member has a cup-like or conical frustum-shape, and wherein the housing has a conical portion.

24. The method of claim 22, wherein the pressure differential between the upper section and the lower section of the housing is created by a negative pressure applied to the upper section of the housing or by a positive pressure applied to the lower section of the housing so that the slit permits fluid flow therethrough.

25. The method of claim 22, wherein the pressure differential between the upper section and the lower section of the housing is created by a positive pressure applied to the upper section of the housing so that the peripheral wall permits fluid flow around the elastomeric member.

26. The method of claim 25, further comprising preventing reflux within the device.

27. The method of claim 22, further comprising:
introducing a flushing solution to the upper portion of the housing via the first opening;
causing, by positive pressure, deflection of the peripheral wall from the housing;
urging the flushing solution around the elastomeric member;
redirecting fluid flow in the lower section of the housing; and
cleaning at least a portion of the lower section of the housing.

28. The method of claim 27, wherein the cleaning further comprises preventing thrombus or bacterial growth within the device after aspiration of biological fluid through the device.

29. The method of claim 22, further comprising flushing of elastomeric member portions contacted with bodily fluids, the method further comprising:
tapering a portion of the lower section of the housing such as to provide turbulences and/or fluid flow direction.

30. The method of claim 25, further comprising maintaining the closure of a slit in the valve, wherein the top surface of the elastomeric member has one or more fluid channels terminating at a peripheral edge of the top surface, the method further comprising:
providing a slit that is formed by a single slit to the elastomeric member;
forming at least two fluid channels orthogonal with a longitudinal axis of the single slit.

* * * * *